(12) United States Patent
Guck et al.

(10) Patent No.: US 10,571,387 B2
(45) Date of Patent: Feb. 25, 2020

(54) APPARATUS AND METHOD FOR DETERMINING THE MECHANICAL PROPERTIES OF CELLS

(71) Applicant: Zellmechanik Dresden GmbH, Dresden (DE)

(72) Inventors: Jochen Guck, Leipzig (DE); Oliver Otto, Dresden (DE); Philipp Rosendahl, Dresden (DE)

(73) Assignee: Zellmechanik Dresden GmbH, Dresden (DE)

( * ) Notice: Subject to any disclaimer, the term of this patent is extended or adjusted under 35 U.S.C. 154(b) by 683 days.

(21) Appl. No.: 14/913,699

(22) PCT Filed: Jun. 26, 2014

(86) PCT No.: PCT/EP2014/063532
§ 371 (c)(1),
(2) Date: Feb. 23, 2016

(87) PCT Pub. No.: WO2015/024690
PCT Pub. Date: Feb. 26, 2015

(65) Prior Publication Data
US 2016/0202172 A1 Jul. 14, 2016

(30) Foreign Application Priority Data
Aug. 23, 2013 (GB) .................................. 1315196.4

(51) Int. Cl.
| G01N 15/14 | (2006.01) |
| B01L 3/00 | (2006.01) |
| G06K 9/00 | (2006.01) |
| G06T 7/00 | (2017.01) |
| G01N 15/00 | (2006.01) |

(52) U.S. Cl.
CPC .... *G01N 15/1475* (2013.01); *B01L 3/502753* (2013.01); *G06K 9/00134* (2013.01); *G06T 7/0012* (2013.01); *B01L 2200/10* (2013.01); *B01L 2300/0636* (2013.01); *G01N 2015/0065* (2013.01); *G01N 2015/149* (2013.01)

(58) Field of Classification Search
None
See application file for complete search history.

(56) References Cited

U.S. PATENT DOCUMENTS

| 3,761,187 A | 9/1973 | Dittrich et al. |
| 4,428,669 A | 1/1984 | Bessis |
| 5,798,827 A | 8/1998 | Frank et al. |
| 6,522,781 B1 | 2/2003 | Norikane et al. |
| 2006/0119836 A1 | 6/2006 | Ku |
| 2007/0008528 A1 | 1/2007 | Chiou et al. |
| 2012/0315690 A1 | 12/2012 | Di Carlo et al. |
| 2013/0177935 A1 | 7/2013 | Di Carlo et al. |

FOREIGN PATENT DOCUMENTS

| DE | 1815352 A1 | 1/1971 |
| WO | WO 99/44488 A2 | 9/1999 |

OTHER PUBLICATIONS

Hou, Han Wei, et al. "Deformability study of breast cancer cells using microfluidics." Biomedical microdevices 11.3 (2009): 557-564.*
Huh, Dongeun, et al. "Microfluidics for flow cytometric analysis of cells and particles." Physiological measurement 26.3 (2005): R73.*
Gossett et al: "Deformability Cytometry: High-Throughput, Continuous Measurement of Cell Mechanical Properties in Extesional Flow", 14th International Conference of Miniaturized Systems for Chemistry and Life Sciences, Oct. 3, 2010, pp. 1382-1384, XP008163341.
Piccardi et al: "Background Subtraction Techniques: A Review", Systems, Man and Cybernetics, 2004 IEEE International Conference on, IEEE, Piscataway, NJ, USA, vol. 4, Oct. 10, 2004, pp. 3099-3104, XP010773231.
J. Guck et al., "Optical Deformability as an Inherent Cell Marker for Testing Malignant Transformation and Metastatic Competence", Biophys. J., vol. 88:5, pp. 3689-3698, May 2005.
J. Guck et al., "The Optical Stretcher: a novel laser tool to micromanipulate cells", Biophysical Journal, vol. 81, issue 2, pp. 767-784, 2001.
Dupire et al., "Full dynamics of a red blood cell in shear flow", Proc. Natl. Acad. Sci. USA, vol. 109, No. 51, pp. 20808-20813, 2012.
D. Gossett et al., "Hydrodynamic stretching of single cells for large population mechanical phenotyping", Proc. Natl. Acad. Sci. USA, vol. 109, No. 20, pp. 7630-7635, 2012.
D.H. Ballard, "Generalizing the Hough Transform to Detect Arbitrary Shapes", Pattern Recognition, vol. 13, No. 2, pp. 111-122, 1981.
E. Smistad et al., "Real-time gradient vector flow on GPUs using OpenCL", J. Real-Time Image Proc., Jun. 2012.
L.A. Herzenberg et al., "The History and Future of the Fluorescence Activated Cell Sorter and Flow Cytometry: A View from Stanford", Clinical Chemistry 48:10, pp. 1819-1827, 2002.

(Continued)

*Primary Examiner* — G Steven Vanni
(74) *Attorney, Agent, or Firm* — Wolf, Greenfield & Sacks, P.C.

(57) ABSTRACT

The present invention relates to a method and an apparatus for sorting cells. The apparatus for determining the mechanical properties of cells comprises: —a microfluidic channel having an inlet and an outlet, the channel being configured to let a fluid containing cells pass therethrough, —a means for introducing a fluid containing cells into the channel so as to establish a flow of the fluid within the channel, —a cell shape measurement device arranged to obtain information of a deformed shape of a cell deformed due to the flow pattern created by the interaction of the fluid flow with the channel, and —an analysis means arranged to use data from the cell shape measurement device to obtain mechanical properties of the cells.

19 Claims, 6 Drawing Sheets

(56) References Cited

OTHER PUBLICATIONS

Willert et al. "Pulsed operation of high-power light emitting diodes for imaging flow velocimetry", Measurement Science and Technology, 21(7):075402 (2010).

Suzuki S. et al., "Topological structural analysis of digitized binary images by border following", Computer Vision, Graphics and Image Processing, 46:32-46 (1985).

A.E. Ekpenyong et al., Viscoelastic Properties of Differentiating Blood Cells are Fate- and Function-Dependent, PLoS One, 7(9), 2012.

* cited by examiner (A)  (B)  (C)

(A)          (B)          (C)

APPARATUS AND METHOD FOR DETERMINING THE MECHANICAL PROPERTIES OF CELLS

RELATED APPLICATION

This application is a national stage filing under 35 U.S.C. 371 of International Patent Application Ser. No. PCT/EP2014/063532, filed Jun. 25, 2014, the content of which is incorporated herein by reference in its entirety.

TECHNICAL FIELD

The present invention relates to an apparatus and a method for determining the mechanical properties of cells.

BACKGROUND ART

It is well known that the mechanical properties of cells contain important information about their state and their function. For example, cancerous cells are more deformable than non-cancerous cells, and also, among cancerous cells, metastatic cancerous cells are more deformable than less aggressive cancerous cells (cf. J. Guck et al., "Optical Deformability as an Inherent Cell Marker for Testing Malignant Transformation and Metastatic Competence", Biophys. J., vol. 88:5, p. 3689-3698, May 2005).

It follows from the above that it is of high importance to determine the mechanical properties of cells. Here, mechanical properties encompass properties such as the Young's modulus, the shear modulus, the viscosity, . . . . However, the above term is not limited to such quantities, and it also encompasses any physical quantities which describe the mechanical behavior of cells. Such a quantity could, e.g., be the relative deformation of a cell compared with its initial shape when subjected to a particular force.

Given their size, it is also evident that macroscopic methods cannot be used for determining the mechanical properties of cells. Therefore, in the prior art, several methods have been proposed for measuring these properties.

One such method is micropipette aspiration. The method of micropipette aspiration makes use of micrometer scaled pipettes to probe the mechanical properties of single cells. The invention goes back to the year 1954 when Mitchison and Swann used a device called the "cell elastimeter" to measure the membrane properties of urchin eggs which have diameters of about 200 μm, Later, smaller pipettes were used: Typical diameters range from 1 to 10 μm. The pipette is mounted on a micromanipulator inside a chamber that contains the sample. The micromanipulator can move the pipette along three axes to grab cells and manipulate them by applying a suction pressure. The sample chamber is observed using a microscope and a hydrostatic device creates a pressure difference between the chamber and the inside of the pipette. The forces that can be reproducibly generated with micropipettes range from 0.01 nN to $10^4$ nN. The limiting factor for very small forces is the hydrostatic generation of the suction pressure. It is even sensitive to the humidity of the air. The maximal suction pressure is limited by the vapor pressure of water to a value of 96 nN/μm². The force F acting on the cells is given by: $F = \Delta P \pi R_P^2$ where $R_P$ is the radius of the pipette tip and $\Delta P$ is the suction pressure.

A further way of determining the mechanical properties of individual cells is by using an atomic force microscope (AFM), which was developed in 1986 by Binning, Quate and Gerber. It is a descendant of scanning tunneling microscopes that relied on electrically conducting surfaces. In contrast the AFM feels the surface with a tip by mechanical forces. This makes the method appropriate to a lot of samples, such as, for example, biological tissues or single cells. Scanning tunneling microscopy and atomic force microscopy have in common that the spatial resolution does not have the limitations of a light microscope.

The central part of an AFM is the cantilever. It is basically a beam with an attached tip or, in particular for measurements of cell mechanics, a bead. The force acting on the cantilever is determined by observing the deflection of the cantilever with a reflected laser beam.

A further method for determining the mechanical properties of cells is the optical stretcher developed by Guck et al., which is described in the paper "*The Optical Stretcher: a novel laser tool to micromanipulate cells*", J. Guck et al., Biophysical Journal, vol. 81, issue 2, pages 767-784, 2001. The optical stretcher makes use of the momentum transfer that happens if a light ray penetrates the surface of an object having a higher or lower refractive index than the surrounding medium.

This principle can be applied to suspended cells in optical traps, since they have a refractive index different from the surrounding medium. In the optical stretcher the cells are held in an optical trap formed by two counter-propagating high power near-infrared laser beams. These beams are exactly opposed and—in contrast to other optical traps—not focused but divergent. Since the two beams have the same intensity there is a stable trapping position in the center between the fiber ends. The principle of the optical stretcher was published in 1999 by J. Guck and J. Käs as WO 99/44488 and proved itself to be highly useful in diagnostic and scientific applications. The optically induced stress is not acting homogeneously on the cell's surface, which is the reason why a deformation of the cell results. This deformation gives an indication of their mechanical properties. Softer cells will deform more under the same stress than stiffer ones. Because the manual evaluation of deformations would be tedious and user biased, a custom automated image processing algorithm was used to quantify the deformation for further analysis.

To do so, the contour of the trapped cell has to be extracted from phase contrast images. Therefore the picture of the cell is transformed into polar coordinates taking into account their almost circular shape. In the transformed image the gradient in a radial direction gives a stable criterion for the position of the cell edge. To smoothen the contour, the contour is transformed into Fourier space, and an inverse transform is carried out whilst neglecting higher order terms. The deformation is quantified by fitting an ellipse to that contour, which allowed for obtaining the lengths of the axes of the ellipse to sub-pixel accuracy.

A further method is to make use of hydrodynamic stretching. There are several microfluidic approaches making use of that principle. Interaction with the flow of the surrounding medium causes stress on the surface of a cell. The forces originate either from a non-zero shear rate of the medium—which causes tangential shear forces—or from inertial momentum transfer—causing forces normal to the object's surface. Momentum transfer only plays a role at higher Reynolds numbers when the inertial terms in the Navier-Stokes-Equations become relevant. In contrast, shear forces are dominant at low Reynolds numbers. The idea behind hydrodynamic stretching is to create a flow field that is able to create enough stress on a cell's surface to cause measurable deformation. Such deformations were observed for red blood cells—which are relatively soft—when flowing through capillaries. However the implementation of hydrodynamic stretching for stiffer cells is challenging. Stiffer cells need higher forces and thus higher flow rates to be deformed measurably. These high velocities make it harder to acquire images of the deformed cells. Further, such approaches, one of which is disclosed in Dupire et al, "Full dynamics of a red blood cell in shear flow", Proc. Natl. Acad. Sci. USA, vol. 109, no 51, pp. 20808-20813, 2012, only infer the cell mechanics indirectly, in this case by the tumbling motion of a cell.

D. Gossett et al., "*Hydrodynamic stretching of single cells for large population mechanical phenotyping*", *Proc. Natl. Acad. Sci. USA*, vol. 109, no 20, pp. 7630-7635, 2012, discloses a method of obtaining mechanical properties of cells by placing them at a point where two counterpropagating liquid flows meet. Due to the momentum change at this point, the cells are distorted, and by making use of an image analysis program, the mechanical properties are evaluated.

This approach requires placing the cells at a point which is unstable due to the two counterpropagating flows. Secondly, the image analysis can only be done after the measurement, since a complicated algorithm is used. This means that it is impossible to analyse the data in real time (i.e. during the measurement), but they have to be stored as a video file only to be analysed later. A consequence of this is that the approach cannot be used for sorting cells according to their mechanical properties. This is because for such a sorting, one needs to determine the properties of a particular cell as it is being transported through the channel, since one has to take a decision as to where to send the cell immediately during the measurement. Since this is impossible in the mechanism proposed by Gossett et al., this is another disadvantage of their method.

U.S. Pat. No. 6,522,781 relates to an apparatus for analyzing particle shapes. That apparatus is not capable of determining the mechanical properties of cells. US 2007/0008528 A1 discloses an apparatus which is reported of being capable of measuring the mechanical properties of cells in real time. However, since it only makes use of an intensity variation of the incident light, the quality of its data is low.

Technical Problem

A problem with most of these prior approaches is that they take a long time to determine the mechanical properties of cells. For example, with the optical stretcher, it is possible to measure the mechanical properties of about 100 cells per hour. Such rates can, however, be too slow for applications where either cells in a dynamical biological state (such undergoing mitosis) need to be studied or a large number of cells need to be analyzed. This is required for example in screening procedures where entire cell populations are treated by biochemical or physical means before being characterized and if required sorted according their mechanical properties. Sorting of cells is e.g. important when correlating mechanical and molecular biological characteristics of cells.

The present invention aims at overcoming these issues. One advantage achieved by embodiments of the present application is that they allow for a real-time analysis of the cells. That is, it becomes possible to obtain optical data of the cells as they are immersed in the fluid flow and to analyse the data as the data are being obtained. i.e. it is not necessary to carry out an offline analysis of the data, which allows for a significant speed-up of the actual analysis. As a consequence, for any given sample of cells, it becomes faster to obtain their mechanical properties after introduction into the apparatus.

One further advantage achieved by embodiments of the present invention is that they allow for sorting of cells according to their mechanical properties as they are transported in a fluid flow, i.e., it is possible to sort cells according to their mechanical properties as they are being led through the apparatus ("real time sorting").

In addition, disadvantages of prior art devices such as that disclosed in US 2007/0008528 A1 are that particles need to be trapped. This makes it complicated to use such an apparatus. The apparatus disclosed in US 2012/0315690 A1 only passively sorts cells by making use of the geometry of the channel which is used. However, the apparatus is not capable of determining that information independently of the channel. In addition, in the apparatus disclosed in that prior art document, sorting was only possible based on a combination of cell mechanics and cell size. I.e., one could not just sort base it on cell mechanics, but was constrained to also take the cell size into consideration.

DISCLOSURE OF THE INVENTION

Some of the above problems are solved by the apparatus according to claim 1.

The apparatus comprises a microfluidic channel having an inlet and an outlet, with the channel being configured to let a fluid containing cells pass therethrough. A microfluidic channel is a channel which has such cross-section dimensions that the cells to be analysed can pass comfortably (i.e. without it being necessary that the cells touch the boundaries of the channel—put differently, the cells do not have to "squeeze through" the channel) through it, at least in those parts of the channel where the measurements are taken. Typical cross-sectional dimensions are 20×20 $\mu m^2$.

However, it is to be understood that these dimensions are non-limiting, and they can be suitably adapted depending on the kind of cells to be analysed. It is also noted that the channel does not have to be uniform. Advantageously, the channel comprises at least one section having an approximately constant cross-section, since in such a section, it is easy to establish a laminar flow, with a corresponding, easily reproducible deformation of the cells.

The apparatus further comprises a device for introducing a fluid containing cells into the channel. This device could, for example, be a syringe pump which has one reservoir arranged for retaining a fluid with suspended cells. This fluid can then ideally be introduced into the channel in a controlled manner so that a flow is established within the channel. Preferably, that flow is arranged to be—at least in parts—laminar, since such a laminar flow allows for a more predictable deformation of cells travelling through the channel. However, also a turbulent flow would be possible, even though then, a quantitative analysis would become more difficult.

The apparatus further comprises a cell shape measurement device. This device obtains data regarding a deformed shape of the cell, which is then sent to an analysis means, which could, e.g., be some kind of computer or even just a microprocessor. Importantly, the deformation of the cell measured by the cell shape measurement device is caused by the flow pattern generated by the interaction of the fluid flow with the channel. One example of such a flow pattern could be an approximately laminar flow, which frequently results in an approximately parabolic flow pattern. This flow occurs at low Reynolds numbers. Another type of flow profile, which occurs at high Reynolds numbers, is turbulent flow. In both of these cases, a flow pattern is generated by the fluid flowing through the channel. This pattern can, in principle, be predicted by solving the Navier-Stokes equation with appropriate boundary conditions at the channel boundaries. These channel boundaries will slow down or even stall fluid flow (the so-called "no-slip boundary condition"), whereas no such conditions occur in the middle of the channel.

Thus, at least in the case of laminar flow, fluid flow is very slow at the boundaries, but fast close to the centre of the channel. This differential in fluid flow velocity causes stresses on the surface of a cell travelling through that channel, which in turn deforms the cell. It is this deformation which is measured by the present apparatus and which is used to obtain a mechanical property of the cell, since the magnitude of that deformation depends on the deformability of the cell.

This contrasts with the optical stretcher, where the cell is stretched by two lasers, and also with prior art devices which use counterpropagating flows to deform cells which are transported to a point where the two counterpropagating liquid flows hit one another. In contrast, a unidirectional flow is used. An advantage achieved compared to the counterpropagating flows is that the system is much more stable, since the cells do not need to be positioned at an unstable point where two counterpropagating flows encounter one another. Compared with US 2012/0315690 A1, it is possible to always determine the mechanical properties of the cell without having to use a specifically adapted microfluidic channel. Put differently, by having an analysis means, it is possible to obtain mechanical properties of cells independent of the type of cell which is used. Also, in that prior art document, the deformability of the cells is only inferred indirectly through the position and the size of the cells.

Preferably, the channel can be a part of a PDMS chip, a glass capillary or a cuvette. In all of these cases, it is easy to manufacture such a channel.

Whilst we note that in the above, a "conventional" channel is used, in which the boundaries of the channel are made from solid material, also a different definition of a channel can be used. For example, the boundaries of the channel could be defined by a counterpropagating sheath of fluid which surrounds the fluid flow containing cells. This particular example would prevent large cells from adhering to the channel boundaries. Another example would be one where the channel is defined by different approximately laminar flows of fluid flowing in the same direction, with the flows having different velocities. In such a case, only the innermost flow would need to have a cross-sectional dimension which approximately corresponds to that of a cell so as to deform such cells.

Regarding the above, as well as the rest of this invention, the term "cells" denotes biological cells in the usual sense. However, it also encompasses soft colloids, immiscible droplets, vesicles and other synthetic cell mimics.

Preferred embodiments are described in the dependent claims.

It is preferred to have the apparatus set up to determine the mechanical properties of cells as they are being led through the channel (real time analysis). This means that data regarding the images of the cells are not stored to a permanent storage device such as a hard drive but the contour of the cell or its deformation is instead analyzed immediately. This makes it possible to use such an apparatus for sorting heterogeneous populations of cells according to their mechanical properties.

According to a preferred embodiment, a cross-sectional width of the channel is between 5 and 300 µm, preferably between 15 and 40 µm, and a cross-sectional height is preferably between 5 and 300 µm, preferably between 15 and 40 µm. These definitions in terms of height and width apply in particular to a rectangular cross-section. Also, a channel with an approximately circular cross-section can be used. In the case of a circular cross-section, a diameter between 5 and 300 µm, preferably between 15 and 40 µm, is advantageous. The cross-sectional dimensions are advantageous since they allow, for most cells, for a strong deformation, which makes it easy to determine their mechanical properties.

Preferably, the channel comprises a section having an approximately constant cross-section. That is, for at least parts of the channel, it does not taper inwards or outwards. This allows for easily producing a laminar flow within that section, which makes it easy to measure the mechanical properties of cells. It follows from this that it is preferred that the cell shape measurement device measures the deformation of the cell within that section, since it is here that this laminar flow can be easily produced. It is preferred to have a length of that section which is within 25 µm to 20 mm, preferably within a range of 50 µm to 5 mm. Such a length is reasonably short to fit into a usable apparatus, whilst being long enough for the flow pattern to stabilize.

It is preferred to adjust the flow speed in the region of interest to be within 0.01 and 500 m/s, preferably between 0.025 and 0.5 m/s. This has proved to be the best range for obtaining a reliable deformation of the cells. A preferred range of pressures for introducing the fluid would be within the range of 10 mbar to 500 mbar.

It is preferred to have a tapered section as part of the channel, with the tapering being arranged along the direction of flow. Since the tapering will act so as to either widen or compress the flow, this can be used to, on purpose, introduce convergent or divergent flow areas, which can be advantageous for deforming the cells, for example to study their time-dependent mechanical properties.

A particular advantage is achieved when the respective widened end of at least one, preferably both tapered sections are provided at the inlet and outlet end of the channel, respectively. This makes it easier to introduce inlet and outlet tubes into the respective ends of the channel, respectively, which means that the apparatus is easier to use. The respective tapered sections are preferably connected by a section having an approximately constant cross-section. Having this section allows for having a region where an approximately constant flow regime can be established, which makes it easier to obtain high quality measurements.

In a preferred embodiment, the mechanical properties of the cell are determined in real time, i.e., as the cells are being transported through the channel, By doing this, a significant speed-up of the determination of cell properties is achieved, in particular compared with prior art examples where data regarding cell motion was first stored to a storage device only to be analysed later. Further, when coupled with a cell sorting capability to be defined later, it becomes also possible to sort cells as they are being led through a channel, which makes it possible to separate heterogeneous populations of cells from one another.

This advantageous embodiment becomes particularly apparent when using a cell throughput of more than 10 cells/s, preferably more than 1000 cells/s. Using such rates, a large number of cells can be quantified regarding their mechanical properties, which makes carrying out a screening process feasible, even if a large number of cells are being screened.

It is also preferred that the cell shape measurement device comprises an optical device arranged to obtain an optical information regarding a shape of the cell as it travels through the channel. Such an optical device could, e.g., be a CMOS camera, a CCD camera, or a quadrant photodiode. These devices are available at a high quality and at low cost. Further, they provide high quality data without interfering with the cells travelling through the channel, which can be important should it be necessary to use the cells after passing through the apparatus.

It is preferred that the apparatus further comprises an image acquisition device which is arranged so that it can image the cells as they pass through the channel. It is arranged such that, if a cell is present within the region of interest within the field of view of the image acquisition device (which could be a camera or any other type of photosensitive sensor), an image of such a cell is obtained. In practical terms, such an image acquisition device could, e.g., be an optical microscope having a camera attached to it. The images obtained by that device could be grey scale images, or they could equally be any other kind of images (such as RGB images, infrared images, fluorescence images, binary images, Fourier images, . . . ). These image acquisition devices are directed at a "field of view". E.g. in the case of a camera, it is what the camera lens is directed at. In the case of an optical microscope, it is what the objective lens is directed at. That field of view contains one or more "regions of interest", which are those parts of the field of view which are taken into consideration to analyse the properties of cells. It is preferred that at least one region of interest (ROI) is directed towards a section of the channel which has an approximately laminar flow profile.

Having such devices which actually produce image data, i.e. which return an actual image of the cell, provide lots of detailed information about the cell, which can then be analysed. As a result, the data obtained by using such a device has a high quality.

One can also acquire a Fourier transform of the cell by imaging the back focal plane of the objective. This would allow for determining shape changes by altered spatial frequency distributions directly in the Fourier image, which could simplify and speed up deformation analysis, in particular in combination with a quadrant photodiode. Alternatively, one could determine cell shapes based on spatial frequency distributions, which could simplify and speed up shape analysis.

We note that our apparatus can be used for measuring the dynamics of cell deformation when the cells are entering the channel or the relaxation of the cells leaving the channel. This can be done by observing the change of the cell contour as the cell enters or leaves the part of the channel where it is deformed. The deformation dynamics and relaxation can be used to obtain additional rheological information e.g. regarding the viscosity and other time-dependent mechanical properties of the cell.

According to a preferred embodiment, the analysis means obtains an estimate of a cell contour by only considering those pixels as forming part of the contour which have a value corresponding to a predefined change in the brightness value in the image obtained when a cell is passing through the region of interest, when compared with an average image. The average image is obtained as an average of several images obtained of the same region of interest as the one observed by the actual image to be analysed (i.e. several images are taken, and then, an average image is computed from these images). A cell which is present in an image will correspond to a particular change in the brightness at the position of the cell. To obtain an average image it is beneficial to take those images whilst no cells are being led through the channel. However, this is not necessary, and it would also be acceptable if cells are being led through the channel whilst taking those images. This is because, thanks to the motion of the cells, their effect on the average image will be minimal and can be taken out of consideration due to the subsequent steps.

By only considering those pixels, which correspond to a certain change in brightness (which could, in the case of a bright field image, be a reduction in brightness), it is ensured that only those pixels which correspond to a cell are taken into consideration. (For example, in some bright field images, a bright fringe occurs due to diffraction around an image of a cell. Such an artifact is taken out of consideration by the above algorithm.)

Here, the term "estimate" is used to denote that a cell contour may not necessarily be complete, so for example, it could be the case that individual pixels of the contour are missing.

When determining that estimate of a cell contour, only those pixels are considered which have a value corresponding to a certain, preset change in a brightness value of the single image when compared with the average image. That brightness value could, in the case of a greyscale image, be the greyscale image of that particular pixel compared to the corresponding pixel in the average image. It could, however, also be a brightness value of a particular component of light, so it could, for example, be a single one of the RGB or other brightness values of the image.

Here, by only considering those pixels which have a change in the brightness which is larger than a certain threshold value, the problem of the contour detection is significantly simplified. Here, the term "considering" means that only those pixels are potential candidates for forming part of the contour.

The contour itself can be, in a preferred embodiment, determined using a border following algorithm. In such an algorithm, in a preferred embodiment, firstly, a pixel is determined which is at the edge of the pixels which are to be considered. Then, the edge is followed until arriving back at the initial pixel. This method can be run repeatedly on the same image to return all possible contours. Then, preferably, only those contours enclosing an area larger than a certain preset value, which typically corresponds to a typical cell size, are treated as estimates of the actual cell contour. This allows for ignoring dirt particles, which may be present in the channel.

Because of the simplicity of this algorithm, it can be executed very quickly on a computer, compared with prior art contour detection methods such as the Hough-transform (cf. D. H. Ballard, "Generalizing the Hough Transform to Detect Arbitrary Shapes", Pattern Recognition, vol. 13, no 2, pp. 111-122) or the gradient vector flow method (cf. E. Smistad et al., "Real-time gradient vector flow on GPUs using OpenCL", J. Real-Time Image Proc., June 2012). This simplicity results in a significant speed-up of cell contour detection. Therefore, the method can determine the estimate very quickly, and as a result, a large number of cells can be analysed in a short amount of time, compared with the prior art. In addition, since it is possible to carry out a real time analysis of the mechanical properties of cells, it becomes possible to use the apparatus as part of an apparatus for sorting cells according to their mechanical properties.

Based on this estimate of the cell contour, a deformation of the cell contour due to the flow in the channel is determined, and based on this determination, in comparison to some undeformed reference state (which can be either measured before the channel or in most cases assumed to be spherical) the mechanical properties of the cell are calculated.

It is also preferred that, prior to the above step of obtaining the estimate of a cell contour, in a further step a), from an image obtained when a cell is passing through the region of interest (also called "single image"), the average image is subtracted (one could also equally subtract the individual image from the average image). As a result of this subtraction, one obtains a "differential image" where the background of the region of interest has been taken out of consideration. Assuming that the image was ideal, one would now only see those parts of the region of interest which are influenced by the cell (i.e. those parts directly influenced by the cell, and also areas adjacent to it where the visual image will be influenced by the cell diffracting light). However, in practice, other artifacts, e.g. image sensor noise, will be present.

The subtraction can be done in a pixel-by-pixel fashion. I.e., it is possible to subtract, for each pixel in the image, the brightness value of the corresponding pixel from the other image. However, it is also possible to bin a preset number of pixels together and to only subtract or even consider their average value, which would lead to a speed up in the detection procedure. An advantage of computing this differential image is that it speeds up the further analysis procedure, in particular because this step can be executed on a dedicated core or other computing means of the analysis means. Also, the differential image can also obtained by performing the subtraction on a camera, which makes the analysis even faster.

Based on this differential image thus obtained, an estimate of a cell contour is obtained in step b).

In a particularly preferred variant of the above embodiment, a further step is provided during step a). In that further step, the brightness value of those pixels of a differential image whose absolute value is smaller than a certain preset value is set to a token value which is ignored in the determination of the contour during the contour detection step. This has the advantage of making it possible to eliminate noise present in images. As a consequence, the quality of the contour detection is improved.

A preferred variant of the above embodiment measures the fluctuation of the brightness value of a certain pixel over a predetermined time and then sets the preset value based on that fluctuation, in particular preferably as a fixed multiple of that fluctuation. An advantage of this is that using such a value for the preset value allows for a high degree of flexibility in adjusting the apparatus to different operating conditions. Put differently, one does not have to define the preset value in advance. Rather, for each different measurement condition (which might be the particular microfluidic channel or the fluid which is used, or even the temperature of the apparatus), it would always be possible to automatically adjust the preset value to an appropriate value. This gives a higher flexibility in using the apparatus.

In a preferred embodiment, the estimate of the contour of the cell is smoothened. This leads to a better quality of the data, since artifacts can be avoided.

A further preferred embodiment is that the differential image is obtained by taking an absolute value of the difference between individual brightness values when obtaining the difference in step a). This makes carrying out the subsequent calculation easier and faster.

Alternatively, one could also set those values of the difference to a token value which is ignored during subsequent processing if it is apparent that this value would be physically meaningless. E.g. if the presence of a cell corresponds to a decrease in brightness, one could ignore those pixels which have an increase in brightness, or vice-versa. This makes data analysis less sensitive to artifacts.

It is preferred to obtain the deformation of the cell contour by comparing the contour measured within a region of interest where a deformation of the cell occurs with another contour obtained of the same cell at an earlier or later position within the apparatus where no or less deformation occurs. In that way, it is not necessary to have any prior information about the shape of the cell in order to determine its mechanical properties. Rather, it suffices to merely introduce the cell into the apparatus, since the apparatus can then automatically compare a deformed shaped of the cell with a reference shape that shows no or less of a deformation.

Alternatively, one could simply compare an individual cell with an average taken of the contours of cells of the same population taken at an earlier or later position within the apparatus where no or less deformation occurs. This would avoid having to take a separate image of each individual cell before it is introduced into the channel, thereby making the measurement easier.

Alternatively, one could also measure the deformation of the cell within the section of the channel that has an approximately constant cross-section. Here, the shear forces are approximately constant, compared with a tapered region, which makes it easier to reliably measure the properties of the cells.

Alternatively, when no undeformed image of the cell is obtained in the apparatus, one can safely assume that cells in suspension, which do not feel any other forces, are spherical, and use that as the undeformed reference shape.

A further preferred way of realizing the invention would be to have the region of interest disposed such that it falls within the tapered section, preferably completely. Due to the tapering, stronger forces are exerted on the cell due to the fluid flow. Therefore, the deformations are more significant, thus allowing for a better quantification of the mechanical properties of the cell.

It is also preferred that the analysis means is arranged to carry out a step of smoothening the estimate of the contour of the cell. This improves the quality of the data. This could, e.g., be done by performing a Fourier transform on the estimate of the contour, ignoring terms in the Fourier transform of a higher order than a certain threshold value, and performing an inverse Fourier transform on that data.

A preferred way of carrying out the invention is to determine the mechanical properties of the cell using the circularity of the estimate of the contour. This allows for an easy and fast way of determining the deformation of the cell.

In a preferred way of carrying out the invention, the apparatus comprises a pulsed light source (preferably only emitting a single colour of light) which illuminates the region of interest so that cells which pass through that region are illuminated.

The duration of the light pulses is set such that it is shorter than the time scale over which the image acquisition device obtains a single image. Put differently, the duration of a single pulse is shorter than the duration during which, e.g., a shutter of a camera is open or, equivalently, the time over which a sensor of the image acquisition device obtains a single image.

The light source itself could use LEDs for emitting light. These can be switched on and off very rapidly (which is important for pulsed operation), and they produce the correct wavelength once they are turned on, without having to first "warm up".

An advantage of using such a way of illuminating cells is that by the "stroboscopic" illumination, it becomes possible to "freeze" cells in their position. That is, their motion during the time scale over which the image acquisition device obtains a single image can be reduced. This would otherwise lead to problems if cells are transported at high fluid flow velocities, since they would thereby blur the image resulting in artifacts in contour detection.

To account for this shortening of the light pulse, it is preferred that the irradiance (light power on a surface) of the light incident on the sensor of the image acquisition device is increased when compared with the irradiance when using continuous illumination. Using a monochromatic pulsed light source also leads to no chromatic aberrations in the imaging device. Thus, at high fluid flow velocities it is still possible to obtain an image of cells with a well-defined contour. Also the application of a monochromatic pulsed light source eases the combination of the described technology with other experimental methods, e.g. fluorescence imaging.

It is beneficial to increase the irradiance of the light to reduce the amount of noise contained within an image. If the irradiance were not increased, this would have as a consequence that not enough light could be gathered by the image detection device. This would lead to a noisier image, thereby reducing the quality of the data Thus, in summary, these novel features provide an apparatus in which blur due to motion of the cells is reduced, preferably below experimental resolution, whilst at the same time maintaining a high quality of the image data.

Another way of obtaining similar results would be to use an image acquisition device that acquires images at a frame rate of more than 50,000 frames/s, preferably more than 100,000 frames/s. This would be an alternative way of "freezing" the motion of the cells, thereby also reducing blur.

It is also preferred to not only measure the mechanical properties of cells but to also measure their biochemical properties. This could, e.g., be done by using methods such as flow cytometry, which will be discussed later.

It is also preferred to use a sheath flow of fluid around the cells which are introduced into the channel. In such a way, cells could also be deformed by the interaction with the fluid of the sheath flow and it becomes possible to prevent cells from adhering to the channel walls.

An application of an apparatus as defined in one of the preceding claims is the cell sorting apparatus according to claim 27. Here, the information obtained by analyzing cells is used to sort these cells according to their mechanical properties. This is useful to separate heterogeneous populations of cells.

It is preferred that the above apparatus comprises a branched channel provided after an outlet of the microfluidic channel as well as a means for causing the cells to enter into a particular one of the plurality of individual channels which form part of the branched channel, Such a way of sorting cells is particularly easy to implement.

It is preferred that the means for causing the cells being transported by the channel to selectively enter a particular one of the individual channels is an impulse imparting means. That is, a certain mechanical impulse is imparted to the cells to cause them to change their direction of motion so that they enter a particular channel. For example, in the case of a Y-shaped channel, it can cause the cells to enter into one or the other of the respective bifurcations.

In a preferred embodiment, the impulse imparting means could transmit the impulse via the fluid, i.e. without having to physically touch the cells. This would allow for controlling the motion of the cells without touching them, which would prevent them from adhering to the impulse imparting means.

Furthermore, it is preferred that the means for providing an impulse to cells is a means for emitting vibrations, in particular a piezoelectric element. In that way, since vibrations and sound can be easily conducted through a fluid, a very efficient way of transmitting an impulse to cells can be provided. Also, piezoelectric elements only have a small inertia, so it becomes possible to sort cells at a high rate.

It is envisaged to provide an apparatus arranged for sorting cells transported by a fluid flow according to their biochemical properties with an apparatus for sorting cells according to their mechanical properties as defined above. This allows for carrying out several types of cell sorting in a single apparatus.

Here, the determination of the mechanical properties is carried out on the same flow of cells which is also used for the sorting according to their biochemical properties. This allows for a reduction in the complexity of the apparatus.

It is preferred to share the means for sorting the cells and a potential branched channel between the two sorting apparatuses. Again, this makes it possible to reduce the complexity of the apparatus.

The apparatus for sorting cells according to their biochemical properties can be implemented by an apparatus for carrying out flow cytometry, in particular fluorescence activated cell sorting (FACS). Flow cytometry is described, for example, in DE 1 815 352 A1, and relates to methods of counting or otherwise analyzing cells. Fluorescence activated cell sorting is described, for example, in L. A. Herzenberg et al., "*The History and Future of the Fluorescence Activated Cell Sorter and Flow Cytometry A View from Stanford*", Clinical Chemistry 48:10, pp. 1819-1827, and is a means for separating cells according to their biochemical properties. Put differently, cells can be labeled by fluorescent markers that are specific to the expression of certain proteins in these cells. The labeled cells are then irradiated by e.g. a coherent light source of specific wavelength, the fluorescent marker is excited and the cells are then sorted according to their emitted fluorescence signal. Thus, it becomes possible to also distinguish different cells according to their biological, as compared with their biomechanical, properties.

In addition, the above-mentioned problems are solved by the method according to the method claims. Preferred embodiments are described in dependent method claims. Regarding an explanation of their features and of their advantages, we refer to the above explanations.

The features of claim 53 ensure that the dimensions of the channel are chosen such that a substantial deformation is possible, whilst making the channel wide enough to avoid the cells adhering to the surroundings of the channel. In particular, the latter would lead to the channel becoming clogged up by cells, which is to be avoided.

It is also envisaged to use the method of analyzing and/or sorting cells and the corresponding apparatus in order to carry out a screening process, i.e. to analyse a large number of cells for their reaction to certain treatments. The method and apparatus can be used for such purposes, since it allows for a high throughput analysis of cells in real-time.

It is also envisaged to additionally observe the behavior of cells as they transition from a deformed state to an undeformed state. This allows for also determining the viscous properties, since they are directly linked to such relaxation timescales. This is particularly advantageous when carried out in those parts of the channel where the diameter is changing, because here, stronger forces are exerted on the cells, thereby leading to higher deformations.

DETAILED DESCRIPTION

Figure 1:
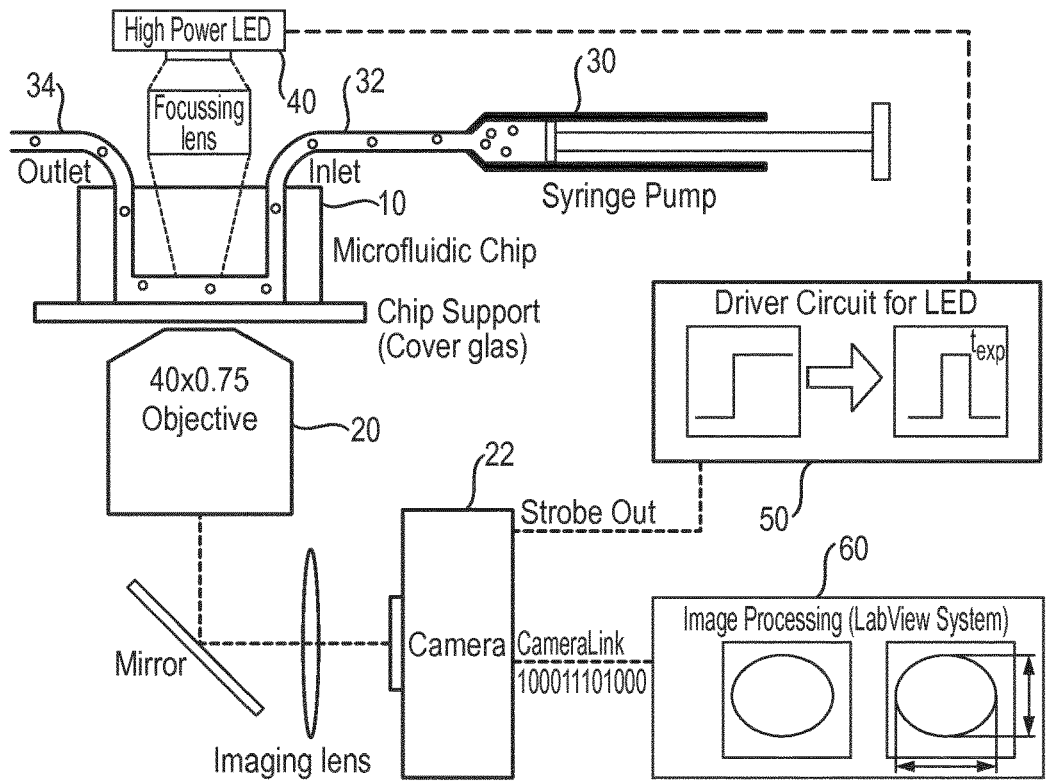
FIG. 1 gives a schematic overview over an apparatus according to the invention.

In the following, we shall describe the setup used for determining the mechanical properties of the cells. An overview is given in FIG. 1. A top view of the microfluidic chip is shown in FIG. 2A.

Figure 2A:
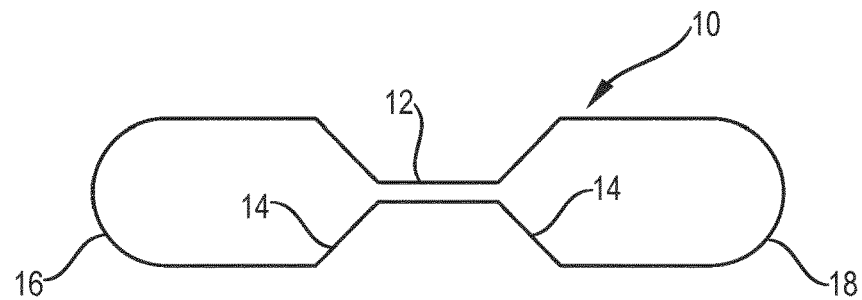
FIG. 2A shows the details of the channel used in the apparatus of FIG. 1.

FIG. 2A shows the design of a microfluidic chip used in the experiments. The total length of the chip is ~2 cm. The two reservoirs 16,18 with a width of 1 mm are connected by a 250 μm long channel section 12 having a width of 20 μm and a square cross-section. Here, we call the assembly of the reservoirs and of the straight channel section a "channel". The "channel section" 12 is the straight part connecting reservoirs 16, 18 via tapered sections 14 and has an approximately constant cross-section. A chrome mask for a lithography process for manufacturing such a chip was printed by the Delta Mask in Enschede, Germany, based on a drawing containing the design of the microfluidic chip.

The geometry of the microfluidic chip was designed with the aim of deforming suspended cells by hydrodynamic interaction and allowing for observation and analysis of the deformation. The aim is to expose the suspended cells to fluid flows of large shear rates to cause a deformation without any surface contact between the cell and the microfluidic chip. Otherwise the channel section would likely be clogged by the suspended cells. The channel section dimensions inside the microfluidic chip need to exceed the diameter of the cells that are measured.

All experiments presented in this application were carried out with HL60 cells which have an average diameter of 12 μm to 15 μm. Therefore a channel section with a cross section of 20×20 μm$^2$ was chosen. This avoids clogging of the channel section and at the same time results in large shear forces due to a large ratio a=cell diameter/channel section diameter ~0.75. The geometry of the chip is defined by the length and diameter of the reservoir, the length and the width of the channel section and the taper angle. In more detail, the channel 10 comprises a channel section 12 having an approximately constant cross-section connected by two tapered regions 14 to an inlet and outlet region 16 and 18, respectively, which are also called reservoirs. In this particular example, the reservoirs (diameter 1 mm, length 5 mm) are connected via a taper of an angle of 45° to the channel section of length 250 μm and width 20 μm. The reservoirs are connected to the inlet and outlet tubings 32, 34, where the inlet tubing 32 is connected to a syringe pump 30 which is arranged to introduce a fluid containing suspended cells into the channel section 12 in a controlled manner.

Starting from a suitable mask a silicon master for PDMS molding based chip production was manufactured using photolithography processes. The following steps describing the workflow to obtain a silicon master have been carried out. Firstly, a silicon wafer is spin coated with a photoresist. Then the mask is used to selectively expose the photoresist layer to UV-light. This triggers a cross-linking reaction in the polymeric photoresist. Therefore the exposed regions are not washed away by the subsequent development step. The resulting wafer with photoresist structures could be used as a casting mold already. To obtain a durable silicon master an additional processing step was performed. Dry etching of silicon using a reactive plasma allows to obtain permanent structures on surfaces with aspect ratios greater than 1. Here, this method was used to etch 20 μm deep structures into the silicon wafer. This step defines the final height of the channel geometry. The structures have angles very close to 90° and there is only minimal surface roughness. To avoid adhesion of the silicon master to PDMS during molding, the surface of the silicon chip was coated with perfluordecyltrichlorosilane (FDTS) rendering the surface hydrophobic.

After surface treatment the silicon wafer is used as a mold for the soft lithography process. Molding was performed using the polymeric material polydimethylsiloxane (PDMS, SYLGARD®, Dow Corning, USA). PDMS is a silicon-based elastomer which is liquid in its native state but solidifies using a chemical cross-linker and heat. PDMS behaves inertly and is biocompatible. Another advantage is its transparency, which allows for observation of the microfluidic channels using a light microscope. For chip production the elastomer and cross-linker are mixed in a ratio of 9:1 (w/w). After extensive stirring and degassing in a vacuum desiccator the mixture is poured onto the silicon casting mold. For polymerization the entire assembly is baked in an oven for 40 min at 60° C. Then the casting mold is carefully peeled off the PDMS piece. To connect the chip to the syringe pump holes are punched into the reservoirs of the PDMS structures using a 1.5 mm hole puncher (Harris UNICORE™, Sigma-Aldrich Chemie GmbH, Taufkirchen bei München). Finally the structured surface of the PDMS piece is to be sealed by a cover glass. This is done by a plasma activation procedure. The structured surface of the PDMS piece and a cover glass (40×25 mm, Glaswarenfabrik Karl Hecht GmbH & Co KG, Sondheim) are cleaned by using Scotch Tape™ (3M Deutschland GmbH, Neuss). After removing dust and dirt, all surfaces were exposed to an atmospheric plasma for surface activation. The plasma cleaner PDC-32G from HARRICK, Pleasantville (USA) was operated for 30 s at "medium" power. Oxidation by the plasma results in silanol groups on the PDMS surface that are highly attractive for the glass surface. Here, the plasma activates the surfaces, since silane groups are present on both PDMS and glass surfaces. As the surface activation decays after some seconds the cover glass is immediately attached to the bottom of the microfluidic chip. This glue free bonding process results in a very stable bond that can resist typical pressures during the experiments.

Figure 2B:
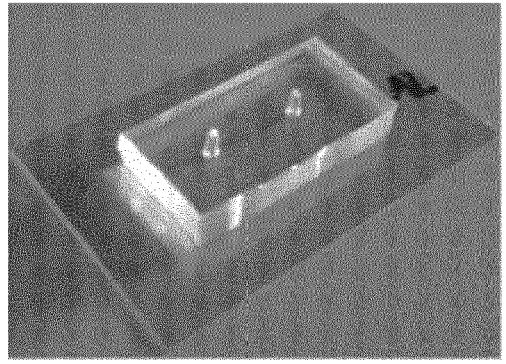
FIG. 2B shows the assembled channel of FIG. 2A.

To pump a cell solution through the chip it has to be connected to the pump. This is done using DuPont®, FEP Fluoropolymer tubings (Postnova Analytics GmbH, Landsberg) with an inner diameter of 0.75 mm and an outer diameter of 1.6 mm. The outer diameter of the tubing is 0.1 mm larger than the inner diameter of the hole in the PDMS leading to a leakproof and pressure resistant connection by simply inserting the tubing a few millimeters into the respective holes of the PDMS chip (cf. FIG. 2B).

In order to observe cells moving through the microfluidic chip a commercially available inverted microscope 20 was used. The Axiovert 200M (Zeiss, Oberkochen) is equipped with a Plan-NEOFLUOAR® 40×NA 0.75 objective lens (Zeiss, Oberkochen). Initial tests verified that a 40×NA 0.75 objective lens, a MC1362 CMOS camera (Mikrotron, Unterschleissheim) and a custom-built light source are an ideal combination for achieving sufficient contrast and brightness for a given field of view covering the whole channel section length of 250 µm. All measurements have been carried out using bright field illumination as phase contrast, dark field and differential interference contrast illumination resulted in a reduced irradiance in the focal plane which was not compensated by the gain in contrast. The microfluidic chip is assembled on the motorized stage of the microscope. During an experiment a cell suspension is pumped through the chip using a syringe pump (neMESYS, cetoni GmbH, Korbwiesen). Illumination is done using a custom-built light source to be described later.

The CMOS camera 22 EoSens CL Camera (MC1362) from Mikrotron, Unterschleissheim, has a full resolution of 1280×1024 and was used in the experiments. For wavelengths between 400 nm and 720 nm the average quantum efficiency of the CMOS sensor is about 40%©. At full resolution the maximum frame rate is 500 frames per second (fps) but for smaller regions of interest (ROIs) the frame rate can be increased to values higher than 100,000 fps. The camera is connected to a standard PC by a National Instruments frame grabber card (NI-1433, National Instruments Germany GmbH, München) via a Full Camera Link interface. The connection has a maximal data rate of 680 MByte/s. For the characterization of the microfluidic chip these high data rates were valuable because they enabled observations of a large region of the channel at high frame rates. After evaluation of full field of view data the ROI was confined to an optimal size for the mechanical measurements to save storage space. For real time data analysis it is important to keep the amount of image data as small as possible to ensure optimal performance. The camera is arranged such that it points towards the region of interest (ROI), which would typically be within the straight section 12 having an approximately constant cross-section or within the tapered section 14 of the channel.

As verified by tests, cells inside the microfluidic channel section 12 move, e.g., at velocities of about 0.163 m/s. This corresponds to a flow rate of about 0.04 µl/s. For cell mechanical measurements images of 300×100 $pix^2$ are sufficient because assuming a 40× objective lens the ROI is sufficiently large to image an entire cell. Considering the pixel magnification of the optical system of 0.34 µm/pix the real dimensions of the ROI have a width of 102 µm and a height of 34 µm. To avoid image artifacts, it is necessary to omit cells that are only partially in the image and overlap with the image border. Assuming a maximal cell radius of 10 µm leads to a margin of that size at the left and right side of the ROI. If the center of mass of a cell is inside this margin, the cell is omitted. Considering these margins, cells moving across the ROI must not move further than 82 µm between two subsequent frames in order to ensure that each cell is imaged entirely at least once. Assuming a velocity of 0.163 m/s a minimal required frame rate to avoid skipping cells can be estimated as 2000/s. The MC1362 camera is capable of operating at such frame rates at a resolution of 300×100 $pix^2$.

In order to yield high light intensities while keeping the exposure time short a pulsed illumination source 40 arranged so as to illuminate the field of view is used which is operated synchronized with the camera shutter. If the pulsed illumination would not be synchronized, it would be difficult to exactly match the frequency of the shutter and the illumination and even small deviations would lead to periodic fluctuations in image brightness. To meet these requirements an illumination source was constructed with the following features:

Sufficient irradiance for short exposure times (down to 1 µs)
Pulsed operation synchronized with camera shutter
Stable irradiance and duration of light pulses
Relatively new in the field of high-power illumination sources are light emitting diodes (LEDs). They are semiconductor based devices consisting of a p-n junction. In contrast to ordinary diodes the recombination of electrons from the conduction band with holes in the valence band leads to the emission of photons of a specific wavelength. As opposed to other illumination sources LEDs do not need to reach a working temperature before they emit light at the specified wavelength and luminance. Therefore they can be switched on and off very rapidly which is necessary for pulsed operation.

Figure 3:
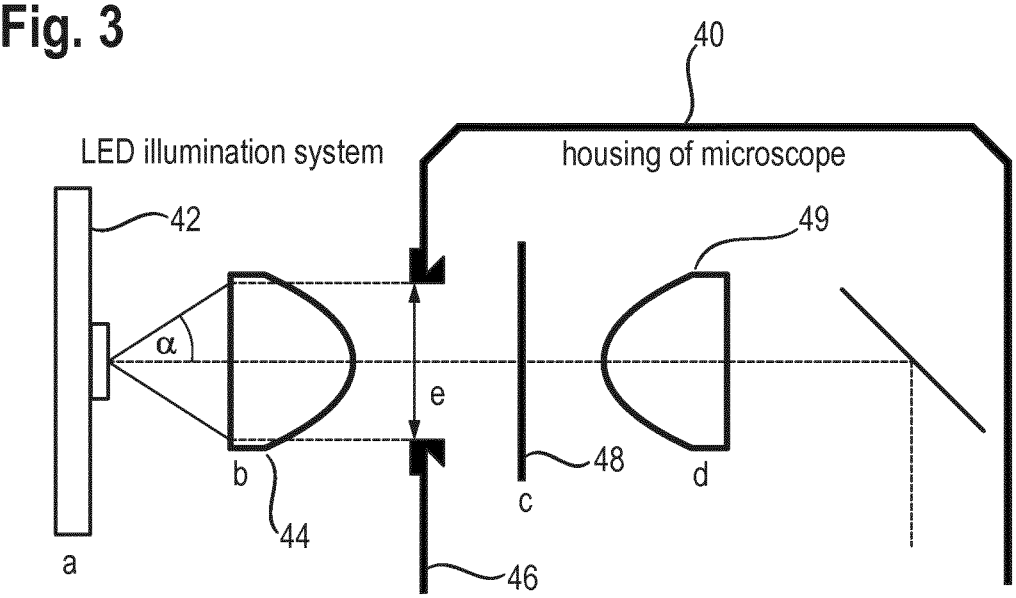
FIG. 3 shows the arrangement used for the light source used in the apparatus of FIG. 1.

A high-power LED 42 was chosen as the optimal illumination source for the experimental setup (cf. FIG. 3). The spectral irradiance exceeds one of a halogen tungsten lamp as well as a mercury arc lamp and meets the requirements of the experimental setup. In addition most mercury arc lamps are operated in AC mode. The resulting fluctuations in irradiance can lead to varying image brightness over time. For bright field illumination the ideal light source does not need to be point-like. In fact a homogeneous light emitting surface that has a size sufficient to illuminate the whole aperture diaphragm is appropriate. In its standard configuration the halogen lamp of the Axiovert 200M microscope has a similar light emitting surface as the selected LED (3×4 mm).

For some years light emitting diodes with a large rectangular light emitting surface have been built for the use in LED projectors. Such LEDs can be driven at very high currents when operated in pulsed mode. When being used as the illumination source of a microscope the effective luminance of such a LED during the short exposure time of some micro seconds is higher than for a tungsten halogen lamp. As no phosphorescent materials are used in this specific LED (in contrast to many modern high-power LEDs) switching on and off times are very short. In fact the rise and fall time is mainly limited by inductive loads in the circuit and in the LED itself and should not be smaller than 0.5 µs to avoid damage to the LED. The CBT-120 LED (Luminus Devices Inc, Billerica, USA) used for the setup has a very high maximum current of 18 A at which it can be driven continuously. At low duty cycles of less than 1% (where the term "duty cycle" denotes how long the current is flowing, compared with the total time of one cycle) the current can be as high as 100 A. If one assumes a forward voltage of 3 V (blue LED) the electrical power consumption of the lamp is about 300 W, which is three times as much as for the substituted halogen tungsten lamp.

Since the LED under consideration (CBT-120, Luminus Devices, USA) is available in different colors, a choice was made considering the spectral response of the camera sensor, the angular intensity distribution of the LED and the diameter of the collector lens. The diameter of the collector lens as depicted in FIG. 3 limits the usable angular range of emitted light. The red version of the LED has a wider light cone than the green and blue ones. The optimal colour for this application was found by multiplying the following factors where each contributes linearly to the signal delivered by the camera: the camera sensor's spectral response at the given wavelength, a correction factor representing the usable portion of the light cone and the total radiometric power of the LED.

The available portion of the total radiometric power was estimated by integrating the spectral irradiance over the usable range of angles. This product is compared for each color. As can be seen in the table below the blue (462 nm) LED has the highest value for the product and therefore is most suitable for the application as tests with different LEDs verified.

| Color | λ (nm) | Spectral response (Vm$^2$/(Ws) | Correction | Radiometric power | Product of response, correction and radiometric power |
|---|---|---|---|---|---|
| Blue | 462 | 4100 | 1 | 10.8 W | 44280 |
| Green | 528 | 5500 | 1 | 4.7 | 25850 |
| Red | 630 | 7000 | 0.87 | 5.8 | 35380 |

The light emitted by LED 42 is incident on a collector lens 44 which condenses the light. The condensed light then enters the microscope via an aperture 46, passes through a diffusor 48 and another condenser 49 to be led towards the field of view.

Figure 4:
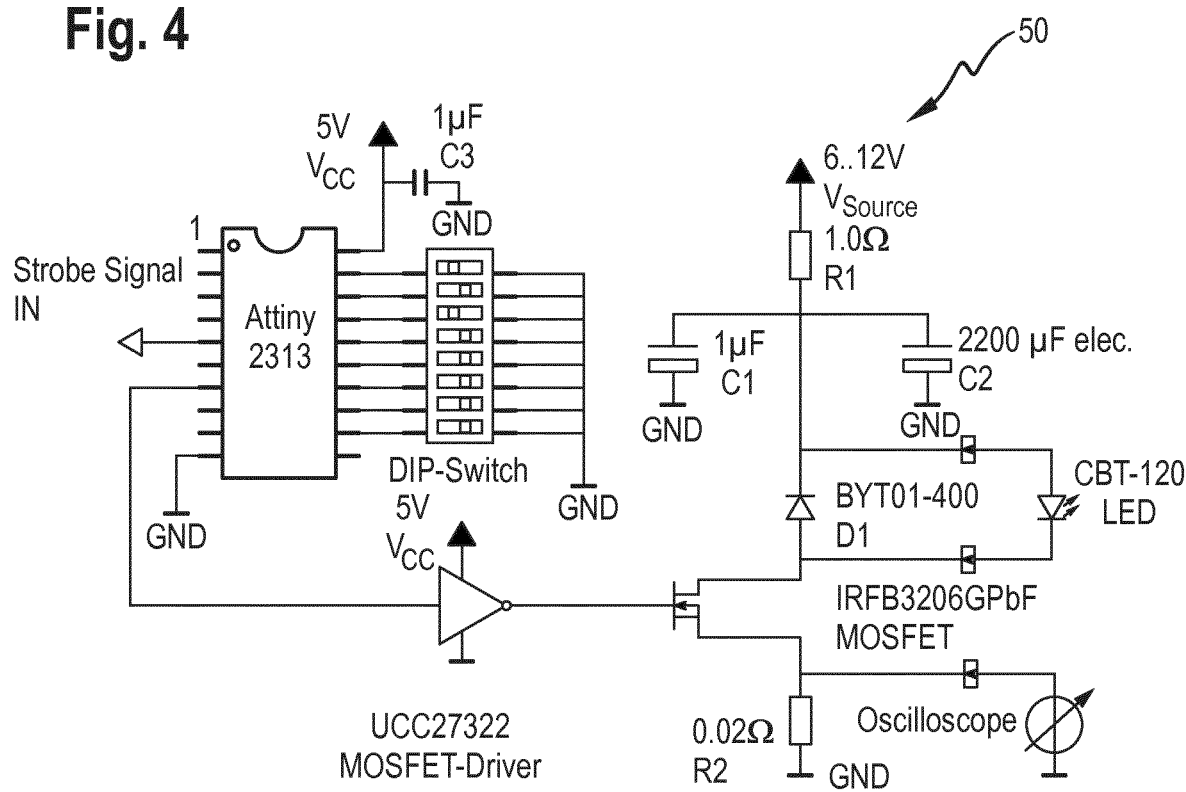
FIG. 4 is a circuit diagram of the controller used for operating the light source shown in FIG. 3.

The driver circuit 50 depicted in FIG. 4 was adapted from Willert, C., Stasicki, B., Klinner, J., and Moessner, S. (2010) "Pulsed operation of high-power light emitting diodes for imaging flow velocimetry" Measurement Science and Technology, 21(7):075402. They have demonstrated the application of a LED-based pulsed illumination source for particle image velocimetry (PIV). As previously discussed the aim is to generate light pulses of 2 µs duration every 0.5 ms (2000 fps), which corresponds to a duty cycle of D=2 ρs/0.5 ms=0.004. Since D is quite small it is not necessary to have a voltage source capable to deliver the full peak current of $I_{peak}$=100 A. Large capacitors with 2200 µF and low resistance are charged between the pulses and allow for a reduction of the supply current by approximately a factor of D. In fact the circuit needs a maximum current of only 2 A at an input voltage of up to 11 V and is able to deliver pulses of up to 100 A. The camera delivers a LVTTL3 signal on the pin "strobe out" which is high as long as the electronic shutter of the CMOS camera is open. This signal will be used to synchronize the illumination source with the camera. It would be possible to set the shutter time of the camera to low values and use the "strobe out" signal to control the LED. But the standard settings of the camera are very long shutter times that could damage the LED that withstands the very high currents only for small duty cycles. To avoid damage to the LED a micro controller based timing circuit was integrated between the strobe signal and the operational amplifier driving the high-current transistor as shown in FIG. 4.

An Attiny2321 (Atmel Cooperation, San Jose, USA) micro controller was programmed to set an output pin to a high state for a time set by a DIP-switch, when a rising edge occurs on the input connected to the strobe signal of the camera. The operational amplifier U1 (shown in FIG. 4) is optimized for driving power MOSFET transistors like T1. These transistors are very efficient in acting like a switch. They can change very fast between being highly conducive and highly resistive, which keeps thermal losses low. The voltage to drive the circuit needs to be significantly higher than the forward voltage specified for the LED $V_f$=4.1 V. This can be traced back to inductive loads present in the circuit. The current has to rise from 0 A to 100 A in microseconds causing voltages that drive opposing currents (Lenz's law). Inductive loads were kept as low as possible using very thick and short wires for critical connections.

Image Analysis

Two principle modes of image acquisition and analysis have to be distinguished: In offline mode all image data are saved and the processing is done after the experiment. In contrast in online (real-time) mode (as presently employed) the analysis of the data is done on the fly and only the information extracted from the cells' contours is stored. Offline mode allows for higher frame rates of up to 10,000 fps whereas for online mode 2,000 fps are sufficient as only one cell is analyzed per frame.

Figure 5:
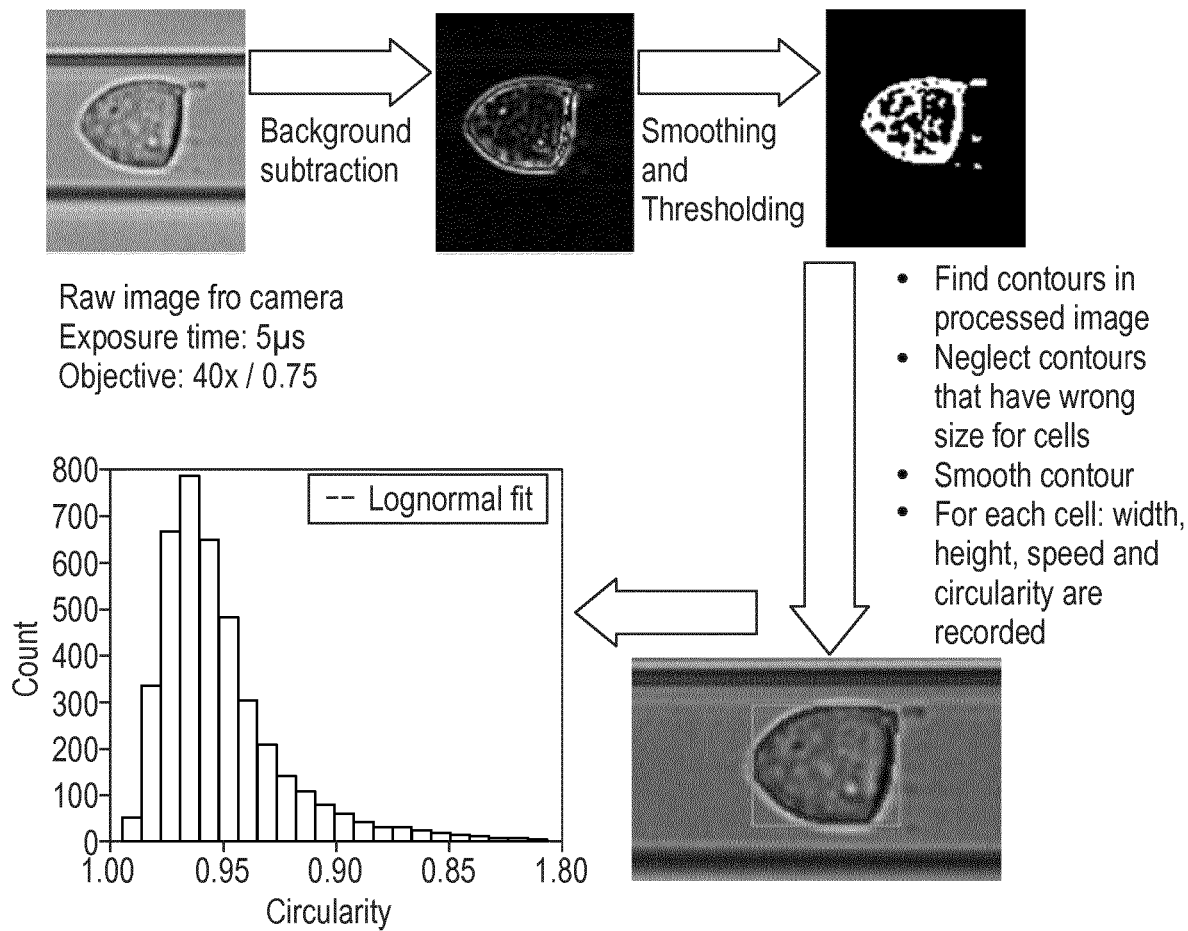
FIG. 5 gives an overview of the image processing algorithm used in the apparatus of FIG. 1.

FIG. 5 summarizes the fundamental steps of image processing independently of its implementation. After image acquisition by the high-speed CMOS camera, a background subtraction is performed. The algorithm checks if there is a cell in the ROI by summation of the pixel values of the background subtracted image. If this sum exceeds a certain threshold the following steps are performed.

Figure 9:
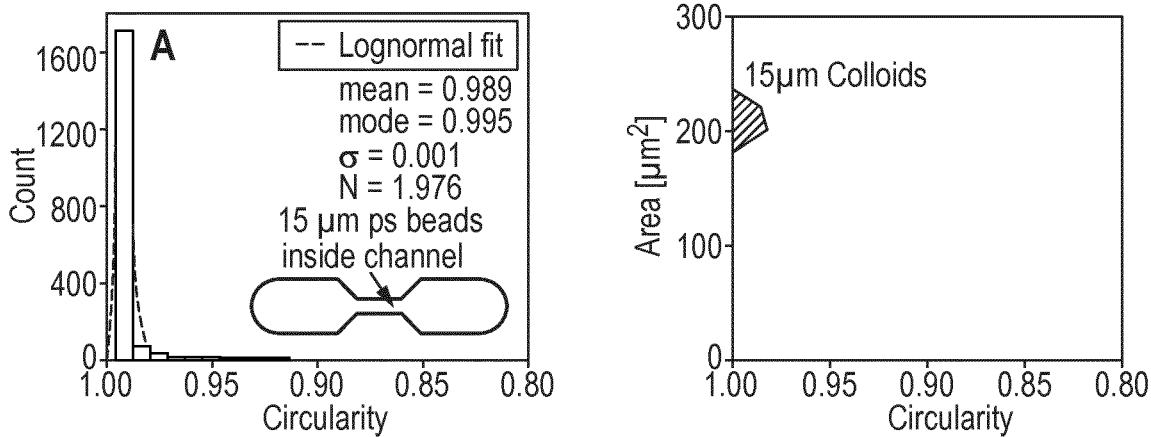
FIG. 9 shows measurement data for polystyrene beads.
Figure 10:
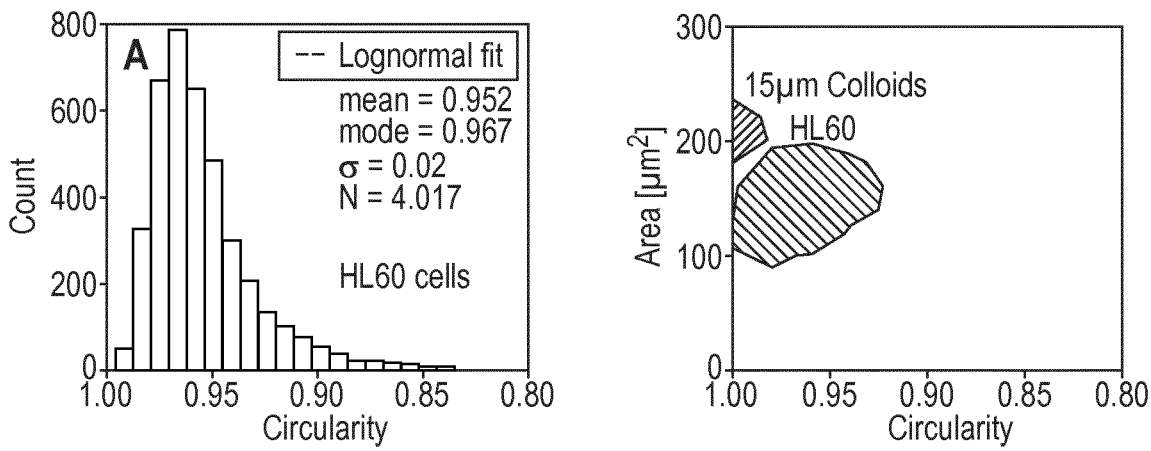
FIG. 10 shows measurement data for HL60 cells.
Figure 11:
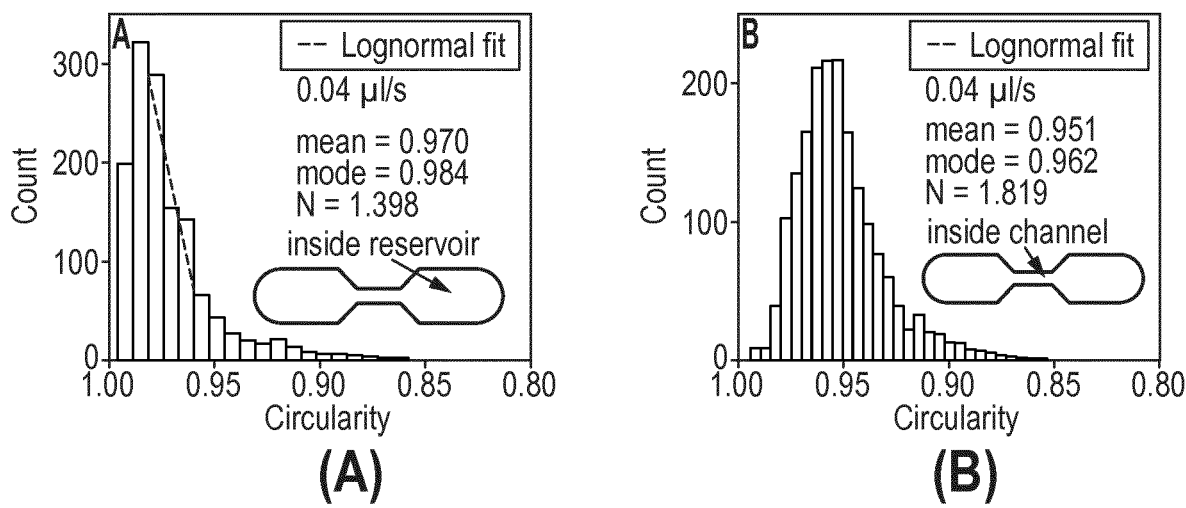
FIG. 11 shows data for HL60 cells obtained for different areas of the channel shown in FIG. 2A.

Application of a thresholding operation on the image reduces background noise and results in a binary image, which is used to determine the contour of the cell, Based on the contour the deformation of the cell can be quantified for each cell. To summarize the measurements of one sample the deformation data is visualized in a histogram or a scatter plot shown in contours (FIGS. 9-11). It has to be emphasized that offline and online operation are based on the same image processing algorithm. For debugging reasons the offline algorithm is implemented as a Python script allowing flexibly changing parts of the program if necessary. On the other hand the real time processing is optimized for performance and implemented in a LabView/C++ environment. The following section describes the image processing step by step.

In order to separate the moving cells from the static background of the video in the image processing a background subtraction is performed as a first step. This is required to remove the channel structures from the images (FIG. 5) that could affect contour detection. Background subtraction is possible because the microfluidic chip does not move during the measurement. As experiments have shown, drift and vibrations can be neglected which means the background is the same for every frame. The only variations of the background are caused by camera noise and instabilities of the illumination source. Background subtraction is performed by a pixelwise subtraction of a background image (which was acquired and stored before) from the image. The background (average) image is acquired by taking the average of about 100 frames. Even if some of these frames contain cells, they won't appear on the average image due to the high number of frames contributing to the averaging. During experiments it is sometimes not possible to gain a background image without cells.

Figure 6:
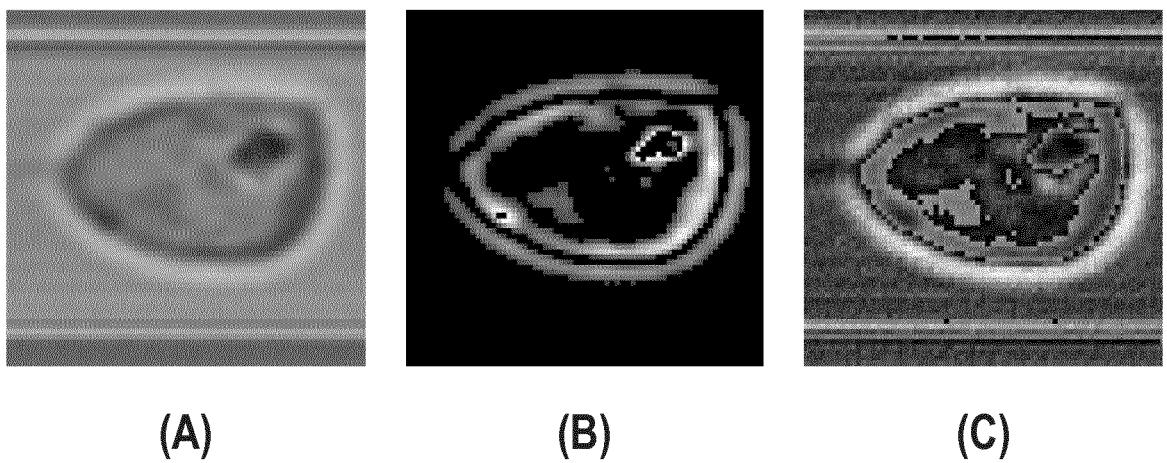
FIG. 6 shows an application example of the algorithm set out in FIG. 5.

In the very left picture of FIG. 6 (subimage (A)) a typical bright field image of a HL60 cell is shown. The cell appears darker than the background and is surrounded by a bright fringe. In fact, whether the cell appears darker or brighter than the background depends on the microscopy method (bright field, phase contrast) and is very sensitive to the relative position of the cell with respect to the focal plane. Thus, two different modes of background subtraction have been tested. The center image in FIG. 6 (subimage (B)) shows a cell after taking the absolute difference of the original image and the background image. Apparently, the channel section walls disappeared while the cell and the inner bright fringe around the cell remains. The handling of this inner fringe is complicated as its appearance is distorted when the cell is close to the channel section wall, which changes the apparent contour. The disturbance of the bright fringe is caused by the channel section walls, which interfere with the illumination. For this reason the bright fringe around the cell shall be neglected. This can be achieved by taking the difference of the background image and the actual image while neglecting all pixels having negative values—those which are brighter in the image than in the background image. The result is shown in the right image of FIG. 6 (subimage (C)). Here, the contour of the cell is very well defined due to the black pixels next to the outer white fringe.

For noise reduction and edge smoothing a convolution of the image and a Gaussian kernel with a width of 3 pix is performed. This smoothing operation is implemented very efficiently by the image library OpenCV. Due to residual noise in the image not all background pixel values are necessarily zero. In order to remove this background noise a thresholding step is performed, which is illustrated in FIG. 7.

Figure 7:
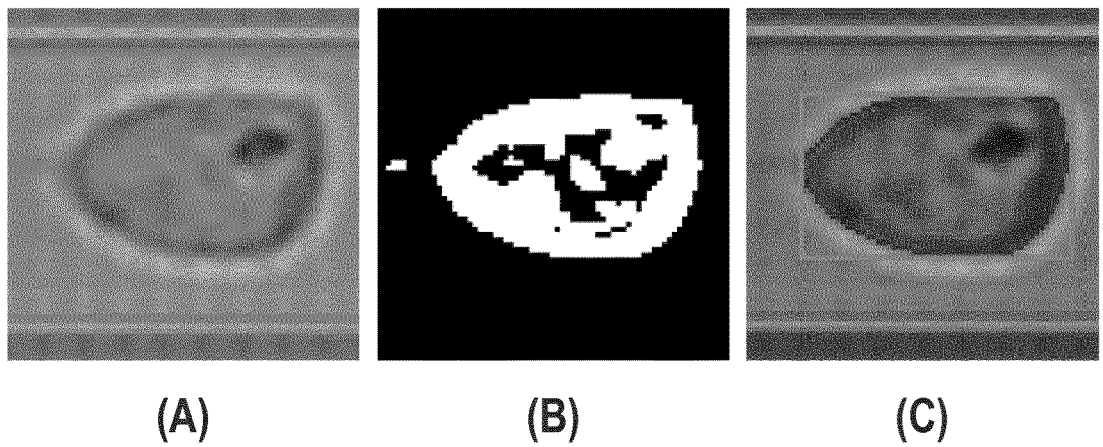
FIG. 7 shows further a detail of the algorithm illustrated in FIG. 6.

After background subtraction of the image shown in FIG. 7, subimage (A), pixels with large values are supposed to belong to the object whereas those with values close to zero are considered to belong to the background. Since there is noise in the picture, the background will not stay constant over time. To simplify contour detection the image is converted into a binary image (FIG. 7, subimage (B)) by performing a thresholding step. All pixels with values below a given threshold value are set to 0 while all remaining are set to the maximum possible value of 255. Now the objects in the image appear as white blobs in the image as shown in the middle image in FIG. 7, subimage (B). The image in FIG. 7, subimage (C) shows the original image (subimage (A)), together with a bounding box and a highlighted contour.

Figure 8:
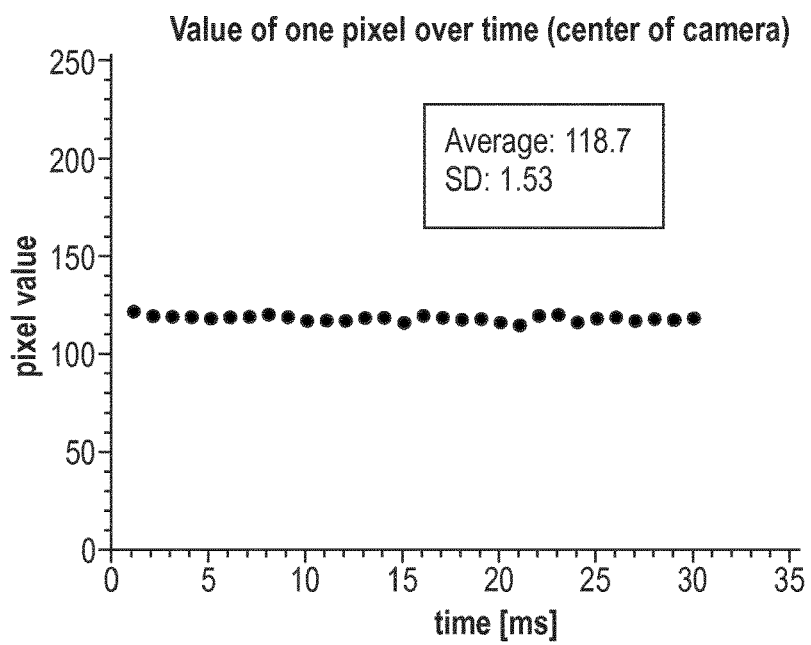
FIG. 8 shows the fluctuation of a single pixel used to determine the inherent fluctuation of the measurements carried out by the apparatus.

In order to quantify noise of a video the value of one pixel in the center was recorded over 20 frames to get an idea of the temporal instability of the brightness. The data is shown in FIG. 8. The deviations from the mean value originate from camera sensor noise and instabilities of the illumination source. For separation of objects from the background a threshold of at least the noise level must be applied after the background subtraction. Although the standard deviation of the noise is below 2 in the present example, threshold values between 5 and 7 have proven to be most efficient in practice. Here, we measure the brightness values on an 8 bit scale, i.e. there are 256 different brightness values. It is these values that the above numbers refer to.

In contrast to contour detection in gray scale images, finding contours in a binary image is a problem which is very well-defined. The algorithm used for this work was taken from the open source image processing library OpenCV. This library contains a large number of basic and advanced image processing functions and is optimized for rapid execution on recent CPUs. The function cv2.findContours( ) (OpenCV library) is an implementation of the Border Following method described by Suzuki in Suzuki, S. (1985), *"Topological structural analysis of digitized binary images by border following"*, Computer Vision, Graphics, and Image Processing, 46:32-46, This algorithm searches for two neighboring pixels with different values. Then it follows the border until the starting point is reached again. The result is a closed contour if the object is not in contact with the image boundaries. Additionally a hierarchy of the determined contours can be returned.

This is not required in here since the algorithm only searches for one contour in an image. Finally, the function cv2.findContours( ) returns a list of all contours found in the image. All contours that are of a size not matching a user defined range are neglected. This step is important as the cell suspension may contain dirt particles which are mostly small compared to cells.

In order to compare the deformation of cells, it is useful to introduce a single parameter to quantify the degree of deformation for each single cell. This can be done in numerous ways.

The circularity of a closed contour is defined by $$C = \frac{2\sqrt{A\pi}}{l}$$

where A is the area enclosed by the contour and l is the perimeter.

The circularity relates the ratio of area and perimeter to that of an ideal circle. For an ideal circle c=1. All other shapes result in values smaller than 1. The circularity does not depend on the absolute size of the contour. For initially spherical cells such as the HL60 cell line the circularity is a very sensitive measure for the induced deformation. However for cells initially having other shapes the circularity may not be the ideal choice, since completely different shapes can lead to the same circularity.

An alternative way of defining circularity is:

$$C = \frac{4A\pi}{l^2}$$

Aspect ratio: If an ellipse is fitted to the contour, the lengths of the major and the minor axis are obtained. The numeric ratio of those axes also quantifies the deformation and is not depending on the absolute size of the cell.

FIG. 7 shows a deformed HL60 cell during an experiment. Although it is slightly stretched along the channel axis its shape is not elliptical.

Roundness: The roundness is defined by taking into consideration a circle in polar coordinates. For an ideal circle this would be a straight line. Thus, when plotting a deformed cell in polar coordinates, a curved line will be obtained. The standard deviation between that curved line and a line representing a circle is called "roundness".

The above parameters have been tested to quantify the deformation of a cell. Some experiments produced deformations into a parachute-like shape, which left the aspect ratio almost unchanged. In contrast, the roundness of the cell does not incorporate the observed area. Therefore, the circularity seems to be the most sensitive and suitable parameter for quantifying the deformation of cells with the microfluidic method.

Contour detection and calculation of circularity is done using the algorithm described above. Real time processing omits storing the image data to a disk and performs all image processing during the experiment in real time Put differently, an image of a cell is recorded by an image acquisition device, analysed for the presence of cells and evaluated before the next image is obtained. No image data needs to be saved to a hard drive or other type of permanent storage device, which also means that such a method is more memory efficient in terms of hard drive space required.

Since the calculations are time critical in this mode, it has to be ensured that processing time for one frame does not exceed the time between two subsequent frames. The performance of LabView's image processing libraries is too poor for these requirements. In order to overcome this bottleneck, the essential parts of the image analysis in C++ were reprogrammed using the OpenCV library. The C++ program was optimized for performance and integrated as a dynamic link library (DLL) into a LabView program for image acquisition. Specific tasks for image processing are dedicated to specific cores of the CPU. The main principle is shown in FIG. 8. Parallelization of calculations results in an increased execution speed, which has proven to be sufficient to analyze up to 100 cells/s in real time (but could be increased further to more than 1000 cells/s).

Figure 5B:
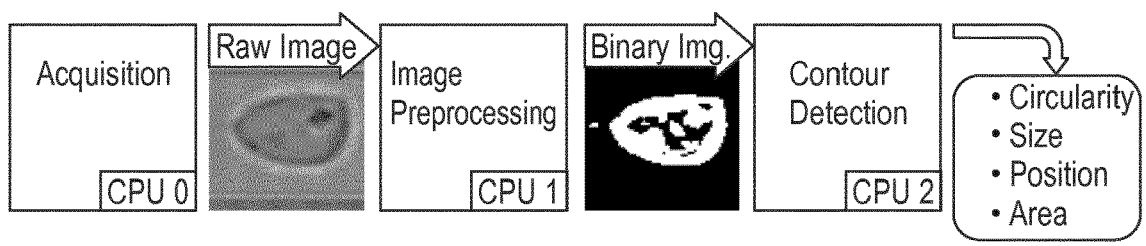
FIG. 5B gives another overview of the algorithm of FIG. 5.

FIG. 5B sketches how each processing step is carried out on a dedicated CPU core, which has been found to lead to a significant speed-up. The raw image data is transferred to a first DLL performing background subtraction and thresholding. This DLL runs on a second core. Transfer of data is done using queues. Subsequently the binary image is handed over to a second DLL running on another core. Here contour detection and calculation of the circularity is performed. Because storing the image data is omitted, the duration of a measurement is not limited by the memory size and only small amounts of data need to be stored. In summary, online processing is capable to deal with one or more ROIs and allows for measurements that are only limited by the sample size.

Evaluation of a Shear Force Acting on a Cell

In the following, one method of estimating the forces acting on a cell is given. It should be noted that this is by no means the only way of obtaining such forces, and numerous other approaches can also be used.

We start by developing a theoretical flow profile for an undisturbed, steady flow in a cylindrical tube with a linear pressure drop between its two ends. This result is modified by changing the boundary conditions to include a moving cylindrical object of infinite length, which is used as a rough model of a deformed cell, centered on the channel axis. The shear stress acting on this object is evaluated considering its dependence on flow velocity, channel geometry and fluid viscosity.

To derive the flow profile inside a cylindrical tube of length L we assume the following:

The channel has a cylindrical shape with radius $r_1$ and length L. Therefore the problem is symmetric under rotations around the x-axis. The velocity field at a point with coordinates (x; y; z) is denoted as u(x; y; z).

The fluid is incompressible.

A pressure difference $\Delta p$ is applied between both ends of the channel of length L. The translational symmetry leads to a constant pressure gradient $\nabla p = \Delta P/L$ along the channel axis.

There are no external forces acting on the fluid, i.e. f=0.

The system has a low Reynolds number Re≤1, which makes the flow laminar and justifies the use of the Stokes-Equation $\nabla p = \eta \Delta u + f$ The fluid velocity u(x; y; z) is zero at the walls of the channel (no-slip boundary)

The Stokes-Equation for stationary flow in Cartesian coordinates without external forces is:

$$\nabla p(r) = \eta \Delta u(r)$$

Exploiting the cylindrical symmetry of the problem the use of cylindrical coordinates (r; $\phi$; x) simplifies the calculations. We note that there are no forces acting on the fluid in other directions than along the x-axis. If one then considers the symmetry of the problem one arrives, after some rearrangements and calculations, at the following equation describing the flow profile:

$$u(r) = u_{max}(r^2/r_1^2 - 1)$$

Note that the pressure gradient is implicitly included in the variable $u_{max}$. In order to estimate the shear stress on the surface of the cell the previously introduced boundary conditions are modified:

A cylindrical object with radius $r_0$ and infinite length is positioned centered around the x-axis. The rotational and translational symmetry is conserved.

The cylindrical object moves with the velocity $u_0$, relative to the channel wall.

The no slip boundary condition is also valid on the surface of the cylinder in the center $u(r_0) = u_0$.

Using the latter condition, we find at the surface of a cell:

$$u_{max} = u_0 \frac{u_0}{\frac{r_0^2}{r_1^2} - 1}$$

if we then consider that the shear stress $\tau$ is given by $$\tau = \eta \frac{du(r)}{dr}$$

with a viscosity $\eta$ we obtain the shear stress $f_0$ acting on a cell surface (which is modeled as a cylinder) as $$f_0 = \frac{\eta u_0 r_0}{r_0^2 - r_1^2}$$

Integrating this over a whole cell surface gives a total force acting on a cell as $$F_{tot} \approx 2\pi r_0 \eta \frac{2u_0 r_0}{r_0^2 - r_1^2}$$

One can use the force thus estimated to obtain a measure of the mechanical properties of the cell by relating it to the deformation of the cell.

Sample Preparation

The following experimental protocol is used for all measurements described in this section. For comparability all studies on HL60 cells presented in this application are carried out during the log phase of cell growth (36 h after splitting). Cells are centrifuged for 5 minutes at 800 rpm (which leads to an outward acceleration of about 100 g) using an Eppendorf 5804 R centrifuge (Eppendorf, Hamburg, Germany). The cells are resuspended in phosphate buffered saline (PBS) containing 0.5% (w/v) methylcellulose. Since a water soluble polymer methylcellulose is used to match the density of the cells and the medium, sedimentation during the experiments is avoided. The final concentration of the cells was adjusted to $1.5 \cdot 10^6$ cells/ml. The viscosity of the medium was measured with a falling sphere viscometer (HAAKE Kugelfallviskosimeter Typ C, Thermo Electron GmbH, Karlsruhe, Germany). At room temperature the viscosity is sixteen times higher than the viscosity of pure water. This leads to higher shear forces at given flow rates compared to PBS buffer only.

The cell suspension is kept at 37° C. before being drawn into a 1 ml-syringe. The syringe is connected to the chip by polymer tubing, which has been extensively cleaned by flushing with ethanol (70%) and 200-nm-filtered deionized water.

The tubing is filled with cell suspension until no air bubbles are present in the system. Finally the tubing is inserted into the hole, which has been punched into the PDMS chip. The chip is mounted on the microscope stage while the syringe is fixed on a syringe pump. The computer-controlled syringe pump (neMESYS, cetoni GmbH, Korbwiesen, Germany) allows for exact control of the flow rate. A typical flow rate used during the experiment is 0.04 µl/s. This flow rate causes an average flow speed of 0.1 m/s in the part of channel which is under consideration (i.e. in the channel section). After starting the flow with the syringe pump, the flow has to stabilize for several minutes due to hydraulic capacitances.

Results

In order to test the general capabilities of the cell tracking software, a control measurement has been conducted using 15 µm sized polystyrene beads (Microparticles, Berlin, Germany). These beads are rigid, thus no deformation by shear should be observed. A circularity of 1 is expected.

All deviations from that value have to be attributed to measurement errors in the imaging and image processing steps.

FIG. 9 shows results of a shear flow experiment, where N=1,976 polystyrene beads have been analyzed in a channel having a channel section of 250 µm length and a cross section of 20×20 µm². The measurement was carried out in a 300×100 pix² ROI in the central part of the channel. A flow rate of 0.04 µl/s was applied, the camera was operated at a frame rate of 2000 fps and the overall measurement took about 120 s. For comparability these parameters have been used in all experiments if not stated otherwise.

The beads are assumed to have perfectly spherical shapes in terms of the resolution of the microscope. The histogram shown in FIG. 9 presents the distribution of circularities, which peaks close to the expected value of 1, but is not distributed symmetrically around this value. In order to determine the maximum of the distribution quantitatively a log-normal probability density function is fitted to this data.

After demonstrating the capabilities of the real time image processing algorithm, experiments with HL60 cells have been carried out. A suspension of HL60 cells was prepared following the protocol previously described. FIG. 10 shows the distribution of circularities for N=4,017 HL60 cells measured in the central part of the 250 µm long channel section. Noticeably, the width of the distribution exceeds the one for the polystyrene beads in FIG. 9. After fitting a log-normal function to the data the histogram reveals a maximum at a circularity of 0.967±0.02. As expected, the circularities are smaller than the one observed for rigid spheres. There is obviously a significant difference between the distributions of the HL60 cells and the beads.

FIG. 10 relates the area and circularity for two different experiments of suspended HL60 cells and 15 µm polystyrene colloids. The widely spread distribution of HL60 cells can be explained by the heterogeneity in cell size which leads to different stresses. Another reason for the variation in size and circularity is found in the hydrodynamic focusing of the cells. Depending on the exact position when entering the narrow channel section the cells deform differently, as was observed. If a cell is very close to the channel section wall the deformation is asymmetric. This issue of proper alignment can be addressed by a focusing method like inertial focusing or a sheath flow geometry.

All experiments presented so far were performed in the section 12 having an approximately constant cross-section of the microfluidic chip 10. In contrast to the channel section the reservoirs have a cross-section of up to 1000×20 µm². Here, the circularity of HL60 cells in the chip reservoir, the channel section and the transition region inbetween (taper) was compared. All experiments observing the transition between the reservoir and the channel section were carried out using offline analysis, but can in principle also be analysed online.

A video is acquired for a large region of interest of 1000 pix×100 pix in order to track the motion of a cell from the reservoir into the channel section. The histograms displayed in FIG. 11 were obtained by analyzing a single video file at different positions of the chip. It is apparent from FIG. 11 that the distribution of circularities depends on the hydrodynamic environment. Histogram (A) represents data acquired from the reservoir while (B) shows results from the channel section. Inside the channel section a peak is found at 0.962±0.02 which is consistent with experiments shown previously. In contrast, the distribution of circularities inside the reservoir peaks at 0.984±0.01. The small deviation from 1 (as expected from colloid measurements) can be explained by the fact that cells are not perfectly spherical but show a heterogeneous distribution of their undeformed shape. Since cells are viscoelastic materials they do not deform instantaneously. The timescale of the deformation depends on its viscoelastic material properties. In order to estimate the time it takes until a cell is deformed, the transition between the reservoir and the channel section was studied qualitatively.

Figure 12:
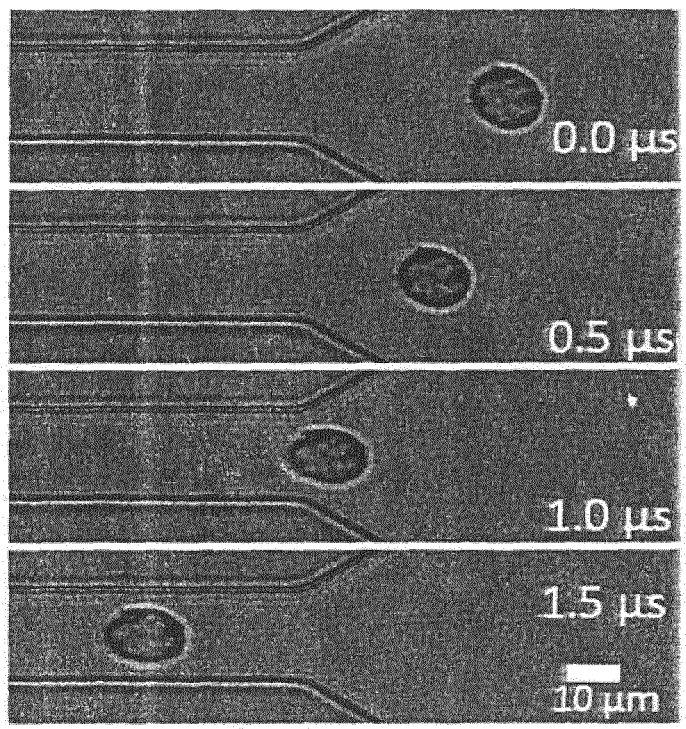
FIG. 12 shows still images of the deformation of a cell as it enters into the channel.

FIG. 12 shows single frames of a cell moving from right to left. When the taper region is observed an initial deformation of the cell into an elliptical shape shortly after entering the channel section becomes apparent. This deformation might be caused by the convergent flow in this region, which could lead to a stress profile squeezing the cell. Usually, the cell resembles its bullet-like shape after it has passed approximately 200 µm of the channel section length. The timescale for this transition from a spherically undeformed shape into the bullet-like shape could be a mechanical marker that is characteristic for heterogeneous cell populations.

Further experiments were carried out using Cytochalasin D treated HL60 cells. This was done to chemically alter the stiffness of the cytoskeleton to demonstrate the sensitivity of the method to different material properties of a cell. First, a suspension of HL60 cells is prepared following the protocol previously described. After resuspension of HL60, 2 mM cytochalasin D are added to a final concentration of 5 µL/ml. The sample is incubated for 10 minutes at 37° C. Cytochalasin D is blocking the polymerization of actin leading to a degradation of the actin filaments in the cytoskeleton and therefore to a softening of the cells, which has been observed for example in optical stretcher experiments.

Figure 10A:
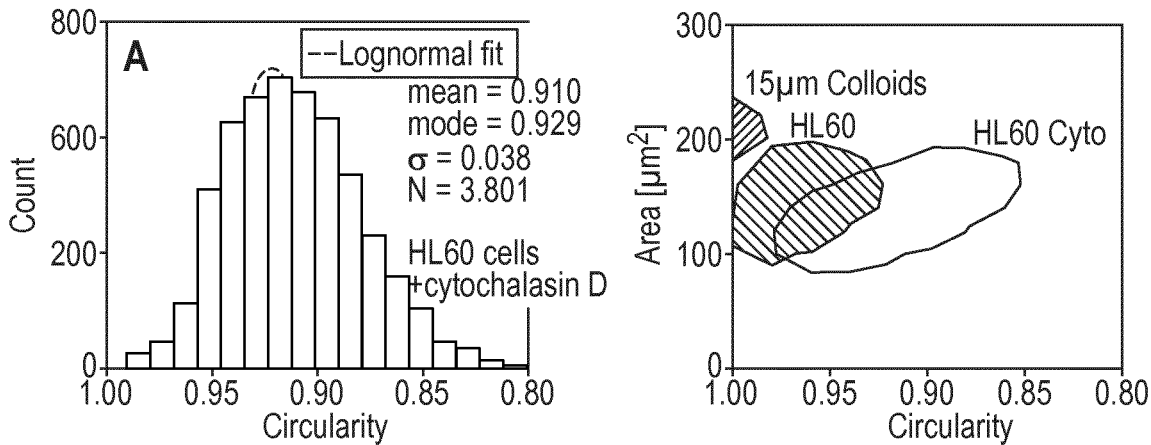
FIG. 10A shows data on cytochalasin D treated HL60 cells for comparison with FIG. 10.

The left histogram in FIG. 10A, which was obtained in a real time measurement, peaks at 0.929±0.04. Clearly, cytochalasin D treated cells deform more for a given flow rate of 0.04 µl/s compared to untreated cells. This is expected and in agreement with previously published data (cf. A. E. Ekpenyong et al., "Viscoelastic Properties of Differentiating Blood Cells are Fate- and Function-Dependent", PLOS One, 7(9), 2012).

The right plot in FIG. 10A compares size and circularity for three different populations of particles. While the 15 µm sized beads are limited to an area of about 200 µm$^2$ and a circularity close to 1, HL60 and cytochalasin D treated HL60 cells show a wider distribution. It has to be emphasized that all experiments have been carried out at the same flow rate of 0.04 µl/s using the same microfluidic chip design. All three populations, although similar in size, can clearly be separated by their circularity. This demonstrates the power of the experimental method in combination with the real time analysis software.

The wide distribution in circularity for treated HL60 cells in the right plot in FIG. 10A can potentially be explained by assuming that the effect of cytochalasin D is not equal to all cells but depends e.g. on cell size and cell cycle stage. In addition, the circularity seems to scale with cell size, i.e. larger cells deform more. This can be understood by the fact that larger cells block a larger cross-section of the channel section. This leads to higher shear forces on the cell.

Further Disclosure

In the above, it was assumed that a contour is traced in an image. However, it is also envisaged that other methods can be used as well to obtain the shape of a cell which is transported in a fluid. For example, a quadrant photodiode can be used as an image acquisition device. If a symmetric cell is disposed directly opposite it, the brightness experienced by all of the individual photodiodes will be approximately the same. In contrast, if a cell is distorted along a particular direction, this will result in a distortion of the brightness distribution which will also be in a particular direction. Thus, it will be possible to also use a quadrant photodiode for the same purpose as the one disclosed above.

Further modifications and alternative embodiments of this invention will be apparent to those skilled in the art in view of this description.

The following numbered items provide further disclosure.
1. Apparatus for determining the mechanical properties of cells, comprising:
    a microfluidic channel (10) having an inlet and an outlet, the channel being configured to let a fluid containing cells pass therethrough,
    a means (30) for introducing a fluid containing cells into the channel (10) so as to establish a flow of the fluid within the channel (10),
    a cell shape measurement device (20, 22) arranged to obtain information of a shape of a cell deformed due to the flow pattern created by the interaction of the fluid flow with the channel (10), and
    an analysis means (60) arranged to use data from the cell shape measurement device (20, 22) to obtain mechanical properties of the cells.
2. Apparatus according to 1, the apparatus being arranged to determine the mechanical properties of the cells as they pass through the channel.
3. Apparatus according to one of 1 and 2, wherein the channel (10) has a cross-sectional width of between 5 and 300 µm, preferably between 15 and 40 µm, and a cross-sectional height is preferably between 5 and 300 µm, preferably between 15 and 40 µm, with the cross-section taken perpendicular to the direction of flow.
4. Apparatus according to one of the preceding items, wherein the channel (10) comprises a section (12) having an approximately constant cross-section, wherein preferably, the cell shape measurement device measures the deformation of the cell within the section (12) having an approximately constant cross-section, the section having an approximately constant cross-section preferably having a length of between 25 µm to 20 mm, preferably within a range of 50 µm to 5 mm.
5. Apparatus according to one of the preceding items, wherein the channel (10) comprises one or more tapered sections, the tapering preferably being arranged along the direction of flow so that the channel either narrows or widens when moving along the direction of flow.
6. Apparatus according to 5, when dependent on 4, wherein there is a first tapered section leading from the inlet of the channel (10) to the section (12) having an approximately constant cross-section, the first tapered section becoming narrower when moving from the inlet to the section (12) having an approximately constant cross-section, wherein there preferably is a second tapered section leading from the section (12) having an approximately constant cross-section to the outlet of the channel (10), the second tapered section becoming wider when moving from the section (12) having an approximately constant cross-section to the outlet of the channel (10).
7. Apparatus according to one of the preceding items, wherein the cell shape measurement device (20, 22) comprises an optical device arranged to obtain an optical information regarding a shape of the cell as it travels through the channel.
8. Apparatus according to 7,
    the optical device being an image acquisition device (20, 22) arranged so as to image cells as they pass through the channel, the image acquisition device (20, 22) being arranged to obtain an image of a region of interest within the channel (10) such that cells present within the region of interest are imaged.
9. Apparatus according to 8,
    wherein the analysis means (60) is arranged to carry out the following steps:
    b) determining an estimate of a cell contour by only considering those pixels as forming part of the estimate of the cell contour which have a value corresponding to a predefined change in the brightness value in the image obtained when a cell is passing through the region of interest, when compared with the average image obtained as an average of several images obtained of the region of interest, and, subsequently, c) determining from the estimate of the cell contour the deformation of the cell contour due to the flow within the channel.

10. Apparatus according to 9, the analysis means being further arranged to carry out, prior to step b), a step a) of obtaining, as a differential image, a difference between an image obtained when a cell is passing through the region of interest and the average image, and using this differential image in step b) for the determination of the cell contour.

11. Apparatus according to 10, wherein the image analysis device is arranged to carry out as part of step a) a further step a1) of setting the values of those pixels of the differential image whose absolute value is smaller than a certain preset value to a value which is ignored in the determination of the contour during step b).

12. Apparatus according to 11, wherein the certain preset value is obtained by:

measuring the fluctuation of a brightness value of a certain pixel or number of pixels over a predetermined time, and calculating the preset value based on that fluctuation, preferably as a fixed multiple of that fluctuation.

13. Apparatus according to one of the items 10 to 12, wherein in step a), when obtaining the difference between an image obtained when a cell is passing through the region of interest and an average image obtained as an average of several images obtained of the region of interest, an absolute value of the difference is used when subtracting the images or where, when the difference has the opposite sign to that which occurs when a cell is present in the image, that pixel is set to a value which is ignored during the determination of the contour.

14. Apparatus according to one of 9 to 13, wherein as part of step c), the deformation of the cell contour is obtained by comparing the cell contour obtained during step b) with a contour of the same cell before or after it is deformed.

15. Apparatus according to one of 9 to 13, wherein as part of step c), the deformation of the cell contour is obtained by comparing the cell contour obtained during step b) with an average contour of undeformed cells of the same type.

16. Apparatus according to one of 8 to 15, when dependent on 5, wherein the region of interest is positioned such that it falls within one of the tapered sections, preferably completely.

17. Apparatus according to one of 8 to 15, when dependent on 4, wherein the region of interest is positioned such that it falls within the section of the channel having an approximately constant cross-section, preferably completely.

18. Apparatus according to one of the preceding items, wherein the deformation of the cell contour is calculated by determining the circularity of the estimate of the contour.

19. Apparatus according to one of the preceding items, wherein the analysis means is arranged to carry out a step of smoothening the estimate of the contour of the cell.

20. Apparatus according to one of the preceding items, the apparatus being arranged to adjust a flow speed of the fluid within the channel at the region of interest to be within 0.01 and 500 m/s, preferably between 0.025 and 0.5 m/s.

21. Apparatus according one of the preceding items, further comprising a light source (40) which is arranged to emit pulsed light towards the region of interest so as to illuminate cells passing through that region, wherein the duration of the light pulses is arranged such that it is shorter than the time over which the cell shape measurement device obtains information of a shape of a single cell.

22. Apparatus according to items 21, the light source being a monochromatic light source, wherein preferably, the irradiance and color of the light emitted by the monochromatic light source is adjusted taking into consideration the sensitivity of the cell shape measurement device and the duration of pulses so that the data obtained has a degree of image noise which is less than or equal to that obtainable by a continuous light source.

23. Apparatus according to one of the preceding items, the apparatus being arranged to also detect biochemical properties by e.g. fluorescence of the cells.

24. Apparatus according to one of the preceding items, wherein the cell shape measurement device is arranged to obtain information of a shape of a cell at a rate of more than 10 measurements/s, preferably more than 1000 measurements/s.

25. Apparatus for determining the mechanical properties of cells according to one of the items, the apparatus further comprising a means for providing a sheath flow of fluid around the fluid containing cells, the sheath flow of fluid being introduced into the channel.

26. Apparatus for measuring the biochemical properties of cells according to one of the items, the apparatus further comprising an apparatus for determining the mechanical properties of cells as defined in one of the previous claims, the apparatus being arranged to measure the biochemical properties of those cells for which the mechanical properties are determined.

27. Apparatus for sorting cells according to their mechanical properties, the apparatus comprising:

an apparatus for determining the mechanical properties of cells according to one of the preceding items, and a means for sorting cells depending on their mechanical properties, the apparatus preferably being arranged to also sort cells according to their biochemical properties.

28. Apparatus according to 27, further comprising:

a branched channel which branches out into a plurality of individual channels, the inlet of the branched channel being provided after an outlet of the microfluidic channel, a means for causing the cells being transported by the fluid to selectively enter a particular one of the plurality of individual channels of the branched channel.

29. Apparatus according to 28, wherein the means for causing the cells being transported by the channel to selectively enter a particular one of the plurality of individual channels of the branched channel is a means for providing an impulse to the cells, wherein the means for providing an impulse to cells is controlled such that it sorts the cells into the plurality of individual channels according to their mechanical properties.

30. Apparatus according to 29, wherein the means for providing an impulse to cells is a means for emitting vibrations, preferably a piezoelectric element.

31. Apparatus for sorting cells being transported by a flow according to their biochemical properties, further comprising an apparatus according to one of 27 to 30 to also sort cells being led through the apparatus for sorting cells according to their biochemical properties,
wherein the determination of the mechanical properties of the cells carried out by the apparatus for determining the mechanical properties of cells is performed on the same flow of fluid which is analysed using the apparatus for sorting cells according to their biochemical properties,
wherein preferably, the means for sorting the cells, including a potential branched channel, is shared between the apparatus for sorting cells according to their biochemical properties and the apparatus for sorting cells according to their mechanical properties, so that it is possible to sort cells according to their mechanical properties whilst also sorting them according to their biochemical properties.

32. Method of determining the mechanical properties of cells, comprising the following steps:
a) providing a flow of a fluid containing cells through a channel,
b) measuring a deformation of a cell due to the flow pattern created by the interaction of the fluid flow within the channel (10), and
c) using the deformation of the cell to obtain mechanical properties of the cell.

33. Method of determining the mechanical properties of cells, comprising the following steps:
a) letting a fluid containing cells pass through a channel (10) so as to produce a flow,
b) obtaining images of the cells as they pass through a region of interest of the channel,
c) determining an estimate of a cell contour by only considering those pixels of the image as forming part of the estimate of the cell contour which have a value corresponding to a predefined change in the brightness value in the image obtained when a cell is passing through the region of interest, when compared with the average image,
d) determining from the estimate of the cell contour the deformation of the cell contour, and
e) calculating mechanical properties of the cell using the deformation of the cell contour.

34. The method of 32,
further comprising, as part of step c), obtaining, as a differential image, a difference between an image obtained when a cell is passing through the channel and an average image obtained as an average of several images obtained of the region of interest, wherein that differential image is used as the image used for determining the estimate of the contour of the cell.

35. The method according to 34, wherein the image analysis device is arranged to carry out, as part of step c), a further step c1) of setting the values of those pixels of the differential image whose absolute value is smaller than a certain preset value to a value which is ignored in the determination of the closed contour during step c).

36. Method according to 35, wherein the certain preset value is obtained by:
measuring the fluctuation of a brightness value of a certain point over a predetermined time, and
calculating the preset value based on that fluctuation, preferably as a fixed multiple of that fluctuation.

37. Method according to one of 33 to 36, further comprising carrying out a step of smoothening the estimate of the contour of the cell.

38. Method according to one of the items 33 to 37, wherein in step c), when obtaining the difference between an image obtained when a cell is passing through the region of interest and an average image obtained as an average of several images obtained of the region of interest, an absolute value of the difference is used when subtracting the images or where, when the difference has the opposite sign to that which occurs when a cell is present in the image, that pixel is set to a value which is ignored during the determination of the contour.

39. Method according to one of 33 to 38, wherein as part of step d), the deformation of the cell contour is obtained by comparing the estimate of the cell contour with a stored contour of the type of cells which are introduced into the channel.

40. Method according to one of 33 to 39, wherein the deformation of the cell is obtained by determining the circularity of the deformed cell.

41. Method of determining the mechanical properties of cells according to one of 32 to 40, the method being arranged to determine the mechanical properties of the cells as they pass through the channel.

42. Method of determining the mechanical properties of cells according to one of 32 to 41, wherein, as part of step c), the deformation of the cell contour is obtained by comparing the cell contour obtained during step b) with a contour of the same cell before or after it is deformed.

43. Method of determining the mechanical properties of cells according to one of 32 to 41, wherein as part of step c), the deformation of the cell contour is obtained by comparing the cell contour obtained during step b) with an average contour of undeformed cells of the same type.

44. Method according to one of 32 to 43, wherein the deformation of the cell contour due to the flow pattern created by the interaction of the fluid flow with the channel (10) is measured in step d).

45. Method according to one of 32 to 44, further comprising the step of emitting pulsed light towards the channel, preferably its region of interest, so as to illuminate cells passing through it,
wherein the duration of the light pulses is arranged such that it is shorter than the time over which a deformation of the cell is measured, preferably shorter than the time during which the image acquisition device obtains a single image.

46. Method according to 45,
the light is monochromatic light,
wherein preferably, the irradiance and color of the monochromatic light is adjusted taking into consideration the sensitivity of the device used for determining the images of the cell and taking into consideration the duration of the pulses so that the data obtained has a degree of image noise which is less than or equal to that obtainable by a continuous light source.

47. Method according to one of 32 to 46, wherein images are obtained or deformations are measured at a rate of more than 10/s, preferably more than 1000/s.

48. Method according to one of 32 to 47, wherein the channel (10) has a cross-sectional width of between 5 and 300 µm, preferably between 15 and 40 µm, and a cross-sectional height of between 5 and 300 µm, preferably between 15 and 40 µm, with the cross-section taken perpendicular to the direction of flow.

49. Method according to one of 32 to 48, wherein the channel (10) comprises a section (12) having an approximately constant cross-section, wherein preferably, the cell shape deformation measurement device measures the deformation of the cell within the section (12) having an approximately constant cross-section, the section having an approximately constant cross-section preferably having a length of between 25 µm to 20 mm, preferably within a range of 50 µm to 5 mm.

50. Method according to one of 32 to 49, wherein the channel (10) comprises one or more tapered sections, the tapering preferably being arranged along the direction of flow so that the channel either narrows or widens when moving along the direction of flow.

51. Method according to 50, when dependent on claim 49, wherein there is a first tapered section leading from the inlet of the channel (10) to the section (12) having an approximately constant cross-section, the first tapered section becoming narrower when moving from the inlet to the section (12) having an approximately constant cross-section, wherein there preferably is a second tapered section leading from the section (12) having an approximately constant cross-section to the outlet of the channel (10), the second tapered section becoming wider when moving from the section (12) having an approximately constant cross-section to the outlet of the channel (10).

52. Method according to one of 32 to 51, wherein the flow speed of the fluid within the channel in the region of interest is within 0.01 and 500 m/s, preferably between 0.025 and 0.5 m/s.

53. Method according to one of 32 to 52, wherein the cross-sectional dimensions of the cell are within 25 and 90%, preferably within 50 and 80%, of the cross-sectional dimension of the channel.

54. Method of sorting cells according to their mechanical properties, comprising the following steps:
  carrying out the method for determining the mechanical properties of cells according to one of 32 to 53, and
  sorting the cells according to their mechanical properties.

55. Method for determining properties of cells, the method comprising carrying out the method of 54, the method further comprising sorting cells according to their biochemical properties, which are preferably measured by fluorescence.

56. Method according to 54 or 55, further comprising:
  providing a branched channel which branches out into a plurality of individual channels, the inlet of the branched channel being provided after an outlet of the microfluidic channel, and
  causing the cells being transported by the fluid to selectively enter a particular one of the plurality of individual channels of the branched channel.

57. Method according to 56, wherein the cells being transported by the fluid are caused to selectively enter a particular one of the plurality of individual channels of the branched channel by providing an impulse to the cells,
  wherein the impulses to cells are controlled such that cells are sorted into the plurality of individual channels according to their mechanical properties.

58. Method according to 57, wherein the impulses are provided by a means of emitting vibrations, preferably by a piezoelectric element.

59. Method of sorting cells according to their biochemical properties, further comprising carrying out a method as set out in one of 55 to 58,
  wherein the sorting of the cells according to their biochemical properties and the sorting of the cells according to their mechanical properties is carried out on the same flow of fluid.

60. The method according to one of 32 to 59, the method being part of a screening process.

61. Use of the method according to one of 32 to 59 or of the apparatus according to one of 1 to 30 for determining the mechanical properties of cells of the following types: prokaryotic cells, eukaryotic cells, animal cells, human cells, blood cells, immune cells, stem cells, cancer cells, tissue cells, genetically modified cells, chemically modified cells, synthetic cell mimics, such as vesicles, immiscible droplets, viscoelastic colloids, and elastic shells.

62. The apparatus or the method according to one of the preceding items, the apparatus or the method being arranged to measure to determine mechanical properties of the cells by observing the transition from a deformed state to an undeformed state and from an undeformed to an deformed state.

The invention claimed is:

1. An apparatus for deforming cells and determining cell contour of the cells, comprising:
  a microfluidic channel having an inlet and an outlet, the channel comprising one or more tapered sections and being configured to let a fluid containing cells pass therethrough,
  a pump configured to introduce a fluid containing cells into the channel so as to establish a laminar flow of the fluid within the channel,
  an optical microscope with attached camera or optical sensor arranged to obtain optical information of a shape of a cell deformed due to the laminar flow pattern created by the interaction of the fluid flow with the channel, wherein the optical microscope with attached camera or optical sensor is arranged so as to image cells as they pass through the channel, and the camera or optical sensor is arranged to obtain an image of a region of interest within the channel such that cells present within the region of interest are imaged, and
  a computer that comprises stored instructions, which instructions are configured to use data from the optical microscope to determine cell contour of the cells, and to carry out the following steps a) and b);
  a) determining an estimate of a cell contour by only considering those pixels as forming part of the estimate of the cell contour which have a value corresponding to a predefined change in the brightness value in the image obtained when a cell is passing through the region of interest, when compared with an average image obtained as an average of several images obtained of the region of interest, and, subsequently,
  b) determining from the estimate of the cell contour the deformation of the cell contour due to the flow within the channel.

2. The apparatus according to claim 1,
  wherein the channel has a cross-sectional width of between 5 and 300 µm, optionally between 15 and 40 µm, and a cross-sectional height is optionally between 5 and 300 µm, optionally between 15 and 40 µm, wherein the cross-sectional width and cross-sectional height are taken perpendicular to the direction of flow and/or
  wherein the channel comprises a section having an approximately constant cross-section, wherein optionally, the optical microscope is configured to measure the deformation of the cell contour within the section having an approximately constant cross-section, the section having an approximately constant cross-section optionally having a length of between 25 µm to 20 mm, optionally within a range of 50 µm to 5 mm.

3. The apparatus according to claim 1, the tapering optionally being arranged along the direction of flow so that the channel either narrows or widens when moving along the direction of flow.

4. The apparatus according to claim 3, wherein there is a first tapered section leading from the inlet of the channel to the section having an approximately constant cross-section, the first tapered section becoming narrower when moving from the inlet to the section having an approximately constant cross-section, wherein there optionally is a second tapered section leading from the section having an approximately constant cross-section to the outlet of the channel, the second tapered section becoming wider when moving from the section having an approximately constant cross-section to the outlet of the channel.

5. The apparatus according to claim 1, the computer further comprising stored instructions, which instructions are configured to carry out, prior to step a),
a step of obtaining, as a differential image, a difference between an image obtained when a cell is passing through the region of interest and the average image, and using this differential image in step b) for the determination of the cell contour,
wherein the computer optionally comprises stored instructions, which instructions are configured to carry out as part of step a) a further step a1) of setting the values of those pixels of the differential image whose absolute value is smaller than a certain preset value to a value which is ignored in the determination of the cell contour during step b),
wherein the certain preset value is further optionally obtained by:
measuring the fluctuation of a brightness value of a certain pixel or number of pixels over a predetermined time, and
calculating the preset value based on that fluctuation, optionally as a fixed multiple of that fluctuation,
wherein, optionally, in step a), when obtaining the difference between an image obtained when a cell is passing through the region of interest and an average image obtained as an average of several images obtained of the region of interest, an absolute value of the difference is used when subtracting the images or where, when the difference has the opposite sign to that which occurs when a cell is present in the image, that pixel is set to a value which is ignored during the determination of the cell contour.

6. The apparatus according to claim 1, wherein the region of interest is positioned such that it falls within one of the tapered sections, optionally completely within one of the tapered sections.

7. The apparatus according to claim 1, wherein the region of interest is positioned such that it falls within the section of the channel having an approximately constant cross-section, optionally completely within the section of the channel having an approximately constant cross-section.

8. The apparatus according to claim 1,
wherein the deformation of the cell contour is calculated by determining the circularity of the estimate of the contour,
and/or
wherein the computer comprises additional stored instructions, which instructions are configured to carry out a step of smoothing the estimate of the cell contour, and/or the apparatus being arranged to adjust a flow speed of the fluid within the channel at the region of interest to be within 0.01 and 500 m/s, optionally between 0.025 and 0.5 m/s,
and/or
wherein the apparatus further comprises a light source which is arranged to emit pulsed light towards the region of interest so as to illuminate cells passing through that region, wherein the duration of the light pulses is arranged such that it is shorter than the time over which the optical microscope obtains information of a shape of a single cell,
wherein the light source optionally is a monochromatic light source,
wherein optionally, the irradiance and color of the light emitted by the monochromatic light source is adjusted taking into consideration the sensitivity of the optical microscope and
wherein the duration of pulses is adjusted so that the data obtained has a degree of image noise which is less than or equal to that obtainable by a continuous light source.

9. The apparatus according to claim 1,
wherein the apparatus is arranged to measure fluorescence of the cells for which the cell contour is determined.

10. The apparatus according to claim 1, further comprising
a flow cytometer provided after an outlet of the microfluidic channel arranged to sort cells depending on cell contour, the apparatus optionally being arranged to also sort cells according to fluorescence,
optionally wherein the flow cytometer further comprises:
a branched channel which branches out into a plurality of individual channels, the inlet of the branched channel being provided after an outlet of the microfluidic channel and
a piezoelectric element configured to cause the cells being transported by the fluid to selectively enter a particular one of the plurality of individual channels of the branched channel,
wherein the piezoelectric element is optionally configured to be controlled such that it sorts the cells into the plurality of individual channels according to the cell contour.

11. The apparatus according to claim 10,
wherein the determination of the cell contour carried out by the apparatus for deforming cells and determining cell contour is performed on the same flow of fluid which is analysed using the apparatus for sorting cells according to fluorescence,
wherein optionally, the flow cytometer is arranged for sort cells depending on cell contour and according to fluorescence and is shared between the apparatus for sorting cells according to fluorescence and the apparatus for sorting cells according to cell contour, wherein cells are sorted according to the cell contour whilst also sorting them according to the fluorescence.

12. A method of deforming cells and determining cell contour of the cells, comprising the following steps:
a) letting a fluid containing cells pass through a microfluidic channel so as to produce a laminar flow to cause a deformation of the cells by the laminar flow pattern created by the interaction of the fluid flow with the channel, wherein the channel comprises one or more tapered sections,
b) obtaining images of the cells using an optical microscope with attached camera or optical sensor arranged to obtain optical information of a shape of a cell deformed due to the laminar flow pattern created by the interaction of the fluid flow with the channel as they pass through a region of interest of the channel to obtain information of a shape of a cell deformed due to the flow pattern created by the interaction of the fluid flow with the channel, c) determining an estimate of a cell contour by only considering those pixels of the image as forming part of the estimate of the cell contour which have a value corresponding to a predefined change in the brightness value in the image obtained when a cell is passing through the region of interest, when compared with the average image, d) determining from the estimate of the cell contour the deformation of the cell contour, and e) determining cell contour using the deformation of the cell contour.

13. The method of claim 12, further comprising, as part of step c), obtaining, as a differential image, a difference between an image obtained when a cell is passing through the channel and an average image obtained as an average of several images obtained of the region of interest, wherein that differential image is used as the image used for determining the estimate of the contour of the cell, wherein optionally a computer comprises stored instructions, which instructions are configured to carry out, as part of step c), a further step c1) of setting the values of those pixels of the differential image whose absolute value is smaller than a certain preset value to a value which is ignored in the determination of the closed contour during step c), wherein the certain preset value is optionally obtained by:
measuring the fluctuation of a brightness value of a certain point over a predetermined time, and
calculating the preset value based on that fluctuation, optionally as a fixed multiple of that fluctuation.

14. The method according to claim 12, further comprising carrying out a step of smoothing the estimate of the cell contour and/or wherein in step c), when obtaining the difference between an image obtained when a cell is passing through the region of interest and an average image obtained as an average of several images obtained of the region of interest, an absolute value of the difference is used when subtracting the images or where, when the difference has the opposite sign to that which occurs when a cell is present in the image, that pixel is set to a value which is ignored during the determination of the cell contour and/or wherein as part of step d), the deformation of the cell contour is obtained by comparing the estimate of the cell contour with a stored cell contour of the type of cells which are introduced into the channel and/or wherein the deformation of the cell is obtained by determining the circularity of the deformed cell and/or the method being arranged to determine the cell contour of the cells as they pass through the channel and/or wherein, as part of step c), the deformation of the cell contour is obtained by comparing the cell contour obtained during step b) with a cell contour of the same cell before or after it is deformed and/or wherein as part of step c), the deformation of the cell contour is obtained by comparing the cell contour obtained during step b) with an average cell contour of undeformed cells of the same type and/or wherein the deformation of the cell contour due to the flow pattern created by the interaction of the fluid flow with the channel is measured in step d) and/or further comprising the step of emitting pulsed light towards the channel, optionally its region of interest, so as to illuminate cells passing through it, wherein the duration of the light pulses is arranged such that it is shorter than the time over which a deformation of the cell is measured, optionally shorter than the time during which a camera or optical sensor obtains a single image, wherein optionally the light is monochromatic light, wherein further optionally, the irradiance and color of the monochromatic light is adjusted taking into consideration the sensitivity of the camera or optical sensor and taking into consideration the duration of the pulses so that the data obtained has a degree of image noise which is less than or equal to that obtainable by a continuous light source.

15. The method according to claim 12, the tapering optionally being arranged along the direction of flow so that the channel either narrows or widens when moving along the direction of flow, wherein, optionally, there is a first tapered section leading from the inlet of the channel to the section having an approximately constant cross-section, the first tapered section becoming narrower when moving from the inlet to the section having an approximately constant cross-section, wherein there optionally is a second tapered section leading from the section having an approximately constant cross-section to the outlet of the channel, the second tapered section becoming wider when moving from the section having an approximately constant cross-section to the outlet of the channel and/or wherein the cross-sectional dimensions of the cell are within 25 and 90%, optionally within 50 and 80%, of the cross-sectional dimension of the channel.

16. The method according to claim 12, further comprising:

sorting the cells according to the cell contour, the method optionally comprising carrying out the method of sorting cells according to the cell contour, the method further comprising sorting cells according to the fluorescence, optionally further comprising:

providing a branched channel which branches out into a plurality of individual channels, the inlet of the branched channel being provided after an outlet of the microfluidic channel, and causing the cells being transported by the fluid to selectively enter a particular one of the plurality of individual channels of the branched channel, the cells optionally being transported by the fluid are caused to selectively enter a particular one of the plurality of individual channels of the branched channel by providing an impulse to the cells, wherein the impulses to cells are controlled such that cells are sorted into the plurality of individual channels according to the cell contour, wherein the impulses are optionally provided by a piezoelectric element.

17. The method of sorting cells according to claim 16, wherein the sorting of the cells according to the fluorescence and the sorting of the cells according to the cell contour is carried out on the same flow of fluid.

18. The method according to claim 12, the method being part of a screening process.

19. The method according to claim 12, wherein the cells are: prokaryotic cells, eukaryotic cells, animal cells, human cells, blood cells, immune cells, stem cells, cancer cells, tissue cells, genetically modified cells, chemically modified cells, synthetic cell mimics, vesicles, immiscible droplets, viscoelastic colloids, or elastic shells.

* * * * *